(12) United States Patent
Rothenberg et al.

(10) Patent No.: US 12,360,103 B2
(45) Date of Patent: Jul. 15, 2025

(54) BLOOD BIOMARKER FOR EOSINOPHILIC GASTROINTESTINAL DISORDERS

(71) Applicant: Children's Hospital Medical Center, Cincinnati, OH (US)

(72) Inventors: Marc E. Rothenberg, Cincinnati, OH (US); Ting Wen, Cincinnati, OH (US); Yrina Rochman, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 1258 days.

(21) Appl. No.: 15/733,755

(22) PCT Filed: Apr. 18, 2019

(86) PCT No.: PCT/US2019/028076
§ 371 (c)(1),
(2) Date: Oct. 16, 2020

(87) PCT Pub. No.: WO2019/204580
PCT Pub. Date: Oct. 24, 2019

(65) Prior Publication Data
US 2021/0080453 A1    Mar. 18, 2021

Related U.S. Application Data

(60) Provisional application No. 62/660,308, filed on Apr. 20, 2018.

(51) Int. Cl.
| A61K 38/35 | (2006.01) |
| A61K 39/00 | (2006.01) |
| G01N 33/50 | (2006.01) |
| G01N 33/68 | (2006.01) |
| C12N 5/0783 | (2010.01) |

(52) U.S. Cl.
CPC ....... *G01N 33/505* (2013.01); *G01N 33/6893* (2013.01); *G01N 2333/5409* (2013.01); *G01N 2333/5437* (2013.01); *G01N 2800/06* (2013.01)

(58) Field of Classification Search
None
See application file for complete search history.

(56) References Cited

U.S. PATENT DOCUMENTS

| 4,376,110 A | 3/1983 | David et al. |
| 4,522,811 A | 6/1985 | Eppstein et al. |
| 4,675,604 A | 6/1987 | Moyer et al. |
| 4,675,904 A | 6/1987 | Silverman |
| 5,015,627 A | 5/1991 | Lindsey |
| 5,148,483 A | 9/1992 | Silverman |
| 5,288,644 A | 2/1994 | Beavis et al. |
| 5,412,073 A | 5/1995 | Kalsheker |
| 5,445,934 A | 8/1995 | Fodor et al. |
| 5,530,101 A | 6/1996 | Queen et al. |
| 5,700,637 A | 12/1997 | Southern |
| 5,744,305 A | 4/1998 | Fodor et al. |
| 5,888,510 A | 3/1999 | Kishimoto et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,403,782 B1 | 6/2002 | Luster et al. |
| 6,429,027 B1 | 8/2002 | Chee et al. |
| 6,733,977 B2 | 5/2004 | Besemer et al. |
| 6,780,973 B1 | 8/2004 | Luster et al. |
| 6,825,350 B2 | 11/2004 | Crooks et al. |
| 6,858,394 B1 | 2/2005 | Chee et al. |
| 7,364,858 B2 | 4/2008 | Barany et al. |
| 7,514,209 B2 | 4/2009 | Dai et al. |
| 7,582,620 B2 | 9/2009 | Lew |
| 7,592,326 B2 | 9/2009 | Karaolis |
| 7,879,547 B2 | 2/2011 | Rothenberg et al. |
| 8,030,003 B2 | 10/2011 | Rothenberg |
| 8,409,565 B2 | 4/2013 | Levi-schaffer et al. |
| 9,260,756 B2 | 2/2016 | Rothenberg et al. |
| 9,345,763 B2 | 5/2016 | Rothenberg et al. |
| 9,517,238 B2 | 12/2016 | Rochman et al. |
| 9,624,545 B2 | 4/2017 | Rothenberg et al. |
| 9,691,411 B2 | 6/2017 | Scherer et al. |
| 9,803,244 B2 | 10/2017 | Rothenberg et al. |
| 9,928,344 B2 | 3/2018 | Rothenberg et al. |
| 9,982,303 B2 | 5/2018 | Rothenberg |
| 10,155,985 B2 | 12/2018 | Rothenberg et al. |
| 10,294,517 B2 | 5/2019 | Rothenberg et al. |
| 10,422,004 B2 | 9/2019 | Rothenberg et al. |
| 10,821,094 B2 | 11/2020 | Azouz et al. |
| 11,564,905 B2 | 1/2023 | Azouz |

(Continued)

FOREIGN PATENT DOCUMENTS

| CN | 101275941 A | 10/2008 |
| EP | 0619321 A1 | 10/1994 |

(Continued)

OTHER PUBLICATIONS

Rochman et al (Science Signaling, 2023, 16.eadg6360, pp. 1-16) (Year: 2023).*
R&D systems (2024, 6 pages) (Year: 2024).*
Khan, S. (Best Practice & Research Clin. Gastroent., 2005, 19(2): 177-198) (Year: 2005).*
Lu et al. (Sep. 15, 2011) "MicroRNA-21 Limits in Vivo Immune Response-mediated Activation of the IL-12/IFN-gamma Pathway, Th1 Polarization, and the Severity of Delayed-type Hypersensitivity", Journal of Immunology, 187 (16):3362-3373.
Lu et al. (Feb. 15, 2013) "miR-223 Deficiency Increases Eosinophil Progenitor Proliferation", Journal of Immunology, 190(4):1576-1582.
Lu et al. (Jul. 2012) "MiR-375 is Downregulated in Epithelial Cells after IL-13 Stimulation and Regulates an IL-13-Induced Epithelial Transcriptome", Mucosal Immunology, 5(4):388-396.

(Continued)

*Primary Examiner* — Michael Szperka
*Assistant Examiner* — Marianne Dibrino
(74) *Attorney, Agent, or Firm* — KDW Firm PLLC

(57) ABSTRACT

The disclosure provides a simple and rapid blood-based bioassay useful in the diagnosis, treatment and monitoring of eosinophilic gastrointestinal disorders, and related compositions and methods.

18 Claims, 18 Drawing Sheets

(56) References Cited

U.S. PATENT DOCUMENTS

| | | | |
|---|---|---|---|
| 2002/0077825 A1 | 6/2002 | Silverman et al. | |
| 2003/0078768 A1 | 4/2003 | Silverman et al. | |
| 2003/0157479 A1 | 8/2003 | Bachmann et al. | |
| 2003/0167189 A1 | 9/2003 | Lutgen et al. | |
| 2003/0194404 A1 | 10/2003 | Greenfeder et al. | |
| 2004/0033502 A1 | 2/2004 | Williams et al. | |
| 2004/0141951 A1 | 7/2004 | Rothenberg et al. | |
| 2005/0163764 A1 | 7/2005 | Medzhitov et al. | |
| 2007/0059720 A9 | 3/2007 | Fuqua et al. | |
| 2007/0233468 A1 | 10/2007 | Ozdas et al. | |
| 2007/0233498 A1 | 10/2007 | Silverman et al. | |
| 2008/0187908 A1 | 8/2008 | Adra | |
| 2008/0201280 A1 | 8/2008 | Martin et al. | |
| 2009/0233275 A1 | 9/2009 | Rothenberg | |
| 2009/0269774 A1 | 10/2009 | Rothenberg et al. | |
| 2010/0151472 A1* | 6/2010 | Nolan | C12Q 1/682 |
| | | | 435/6.1 |
| 2010/0240965 A1 | 9/2010 | Furuta et al. | |
| 2010/0262603 A1 | 10/2010 | Odom et al. | |
| 2011/0123530 A1 | 5/2011 | Arron et al. | |
| 2011/0144183 A1 | 6/2011 | Paquet et al. | |
| 2011/0195500 A1 | 8/2011 | Rothenberg | |
| 2011/0301046 A1 | 12/2011 | Rothenberg et al. | |
| 2012/0004205 A1 | 1/2012 | Rothenberg | |
| 2012/0041911 A1 | 2/2012 | Pestian et al. | |
| 2012/0283117 A1 | 11/2012 | Rothenberg | |
| 2012/0288068 A1 | 11/2012 | Jaiswal et al. | |
| 2013/0035961 A1 | 2/2013 | Yegnanarayanan | |
| 2013/0065972 A1 | 3/2013 | Dent et al. | |
| 2013/0324435 A1 | 12/2013 | Rothenberg et al. | |
| 2014/0073801 A1 | 3/2014 | Storer et al. | |
| 2014/0113372 A1 | 4/2014 | Haque et al. | |
| 2014/0228301 A1 | 8/2014 | Meade et al. | |
| 2014/0228315 A1 | 8/2014 | Rothenberg et al. | |
| 2014/0286896 A1 | 9/2014 | Rothenberg et al. | |
| 2014/0328861 A1 | 11/2014 | Payton et al. | |
| 2014/0343255 A1 | 11/2014 | Gonzalez et al. | |
| 2015/0038552 A1 | 2/2015 | Rothenberg et al. | |
| 2015/0045334 A1* | 2/2015 | Rothenberg | G01N 33/493 |
| | | | 514/169 |
| 2015/0182499 A1 | 7/2015 | Reboud-ravaux et al. | |
| 2015/0355180 A1 | 12/2015 | Resnick et al. | |
| 2016/0129012 A1 | 5/2016 | Rochman et al. | |
| 2016/0177394 A1 | 6/2016 | Rothenberg et al. | |
| 2016/0180041 A1 | 6/2016 | Pestian et al. | |
| 2016/0213681 A1 | 7/2016 | Santus et al. | |
| 2016/0264658 A1* | 9/2016 | Ahmed | A61P 1/12 |
| 2016/0304960 A1 | 10/2016 | Rothenberg | |
| 2016/0312282 A1 | 10/2016 | Rothenberg et al. | |
| 2017/0002021 A1 | 1/2017 | Wagberg | |
| 2017/0061073 A1 | 3/2017 | Sadhasivam | |
| 2017/0067111 A1 | 3/2017 | Rothenberg et al. | |
| 2017/0183719 A1 | 6/2017 | Rothenberg et al. | |
| 2017/0199191 A1 | 7/2017 | Fulkerson | |
| 2017/0233813 A1 | 8/2017 | Rothenberg et al. | |
| 2017/0281716 A1 | 10/2017 | Martin | |
| 2019/0000799 A1 | 1/2019 | Azouz et al. | |
| 2019/0046444 A1 | 2/2019 | Konduri et al. | |
| 2020/0338043 A1 | 10/2020 | Azouz et al. | |

FOREIGN PATENT DOCUMENTS

| | | |
|---|---|---|
| EP | 0619321 B1 | 1/1999 |
| EP | 0949271 A1 | 10/1999 |
| GB | 2450780 A | 1/2009 |
| WO | 8910977 A1 | 11/1989 |
| WO | 9937319 A1 | 7/1999 |
| WO | 2005007175 A2 | 1/2005 |
| WO | 2005033134 A2 | 4/2005 |
| WO | 2005106492 A2 | 11/2005 |
| WO | 2005106492 A3 | 5/2006 |
| WO | 2006083390 A2 | 8/2006 |
| WO | 2006119343 A1 | 11/2006 |
| WO | 2006083390 A3 | 12/2006 |
| WO | 2009015434 A1 | 2/2009 |
| WO | 2009018493 A1 | 2/2009 |
| WO | 2009061819 A1 | 5/2009 |
| WO | 2009089062 A2 | 7/2009 |
| WO | 2009089062 A3 | 9/2009 |
| WO | 2009089062 A8 | 9/2010 |
| WO | 2010126867 A1 | 11/2010 |
| WO | 2012025765 A1 | 3/2012 |
| WO | 2012094643 A2 | 7/2012 |
| WO | 2012094643 A3 | 11/2012 |
| WO | 2012174549 A2 | 12/2012 |
| WO | 2012177945 A2 | 12/2012 |
| WO | 2012178188 A2 | 12/2012 |
| WO | 2012174549 A9 | 2/2013 |
| WO | 2012177945 A3 | 2/2013 |
| WO | 2013082308 A1 | 6/2013 |
| WO | 2012178188 A3 | 7/2013 |
| WO | 2013126834 A1 | 8/2013 |
| WO | 2013155010 A1 | 10/2013 |
| WO | 2014059178 A1 | 4/2014 |
| WO | 2014190269 A1 | 11/2014 |
| WO | 2015017731 A1 | 2/2015 |
| WO | 2015127379 A1 | 8/2015 |
| WO | 2015142739 A1 | 9/2015 |
| WO | 2016023026 A1 | 2/2016 |
| WO | 2016196146 A1 | 12/2016 |
| WO | 2017048860 A1 | 3/2017 |
| WO | 2017123401 A1 | 7/2017 |
| WO | 2019204580 A1 | 10/2019 |

OTHER PUBLICATIONS

Lu et al. (Mar. 22, 2013) "Targeted Ablation of miR-21 Decreases Murine Eosinophil Progenitor Cell Growth", PLoS One, e59397, 8(3):8 pages.

Lucendo et al. (Jun. 15, 2011) "Montelukast Was Inefficient in Maintaining Steroid-Induced Remission in Adult Eosinophilic Esophagitis", Digestive Diseases and Sciences, 56(12):3551-3558.

Lucendo et al. (Sep. 2008) "Treatment with Topical Steroids Downregulates IL-5, Eotaxin-1/CCL11, and Eotaxin-3/CCL26 Gene Expression in Eosinophilic Esophagitis", The American Journal of Gastroenterology, 103 (9):2184-2193.

Zhang et al. (Dec. 2009) "Effects of Endogenous Glucocorticoids on Allergic Inflammation and T(H)1/T(H)2 Balance in Airway Allergic Disease", Annals of Allergy, Asthma & Immunology, 103(6):525-534.

Markowitz et al. (Apr. 2003) "Elemental Diet Is an Effective Treatment for Eosinophilic Esophagitis in Children and Adolescents", The American Journal of Gastroenterology, 98(4):777-782.

Martin et al. (May 2003) "Role of Innate Immune Factors in the Adjuvant Activity of Monophosphoryl Lipid A", Infection and Immunity, 71(5):2498-2507.

Martinez-Nunez et al. (Jan. 21, 2011) "The Interleukin 13 (IL-13) Pathway in Human Macrophages is Modulated by MicroRNA-155 via Direct Targeting of Interleukin 13 Receptor Alpha1 (IL13Ralpha1)", Journal of Biological Chemistry, 286(3):1786-1794.

Matsushima (2010) "MicroRNAs and Esophageal Squamous Cell Carcinoma", Digestion, 82(3):38-144,.

Mattes et al. (Nov. 3, 2009) "Antagonism of microRNA-126 Suppresses the Effector Function of TH2 Cells and the Development of Allergic Airways Disease", Proceedings of the National Academy of Sciences of the United States of America, 106(44):18704-18709.

Mayer et al. (Apr. 27, 2001) "Identification of Receptor Binding and Activation Determinants in the N-Terminal and N-loop Regions of the CC Chemokine Eotaxin", Journal of Biological Chemistry, 276(17):13911-13916.

Mayoral et al. (Jan. 1, 2009) "MicroRNA-221-222 Regulate the Cell-Cycle in Mast Cells", Journal of Immunology, 182(1):433-445.

McGettrick et al. (Sep. 25, 2007) "Toll-like Receptors: Key Activators of Leucocytes and Regulator of Hematopoiesis", British Journal of Haematology, 139(2):185-193.

Medina et al. (Sep. 2, 2010) "OncomiR Addiction in an in Vivo Model of microRNA-21-induced Pre-β-cell Lymphoma", Nature, 467(7311):86-90.

(56) References Cited

OTHER PUBLICATIONS

Meineke et al. (Dec. 2002) "Pharmacokinetic modelling of morphine, morphine-3-glucuronide and morphine-6-glucuronide in plasma and cerebrospinal fluid of neurosurgical patients after short-term infusion of morphine", British Journal of Clinical Pharmacology, 54(6):592-603.
Menard-Katcher et al. (2012) "MicroRNAs are Altered in Eosinophilic Esophagitis", Gastroenterology, 142(5) 8440.
Menzies-Gow et al. (Apr. 2003) "Anti-IL-5 (Mepolizumab) Therapy Induces Bone Marrow Eosinophil Maturational Arrest and Decreases Eosinophil Progenitors in the Bronchial Mucosa of Atopic Asthmatics", The Journal of Allergy and Clinical Immunology, 111(4):714-719.
Meyer et al. (Jan. 2013) "The UCSC Genome Browser database: Extensions and Updates 2013", Nucleic Acids Research, 41:D64-D69.
Michael et al. (2005) "Biochemical and Enzymatic Characterization of Human Kallikrein 5 (hK5), a Novel Serine Protease Potentially Involved in Cancer Progression", Journal of Biological Chemistry, 280(15):14628-35.
Michaels et al. (Feb. 5-11, 2005) "Prediction of Cancer Outcome with Microarrays: A Multiple Random Validation Strategy", Lancet, 365(9458):488-492.
Milbrandt J. (Nov. 6, 1987) "A Nerve Growth Factor-induced Gene Encodes a Possible Transcriptional Regulatory Factor", Science, 238(4828):797-799.
Milgrom et al. (Dec. 23, 1999) "Treatment of Allergic Asthma with Monoclonal Anti-IgE Antibody", The New England Journal of Medicine, 341(26):1966-1973.
Mishra et al. (Jan. 1, 2001) "An Etiological Role for Aeroallergens and Eosinophils in Experimental Esophagitis", Journal of Clinical Investigation, 107(1):83-90.
Mishra et al. (Jan. 2008) "Esophageal Remodeling Develops as a Consequence of Tissue Specific IL-5-induced Eosinophilia", Gastroenterology, 134(1):204-214.
Mishra et al. (Mar. 1, 2002) "IL-5 Promotes Eosinophil Trafficking to the Esophagus", The Journal of Immunology, 168(5):2464-2469.
Mishra et al. (Nov. 2003) "Intratracheal IL-13 Induces Eosinophilic Esophagitis by an IL-5, Eotaxin-1, and STAT6-Dependent Mechanism", Gastroenterology, 125(5)1419-1427.
Mitchell et al. (Jul. 29, 2008) "Circulating microRNAs as Stable Blood-based Markers for Cancer Detection", Proceedings of the National Academy of Sciences of the United States of America, 105(30):10513-10518.
Mizuno et al. (2013) "Genotype of Abcc3-211c > T Influences the Pharmacokinetics of Morphine Glucuronide in Children", Clinical Pharmacology & Therapeutics, 93:S63.
Mogil et al. (Jul. 6, 1999) "The genetic mediation of individual differences in sensitivity to pain and its inhibition", PNAS, 96(14):7744-7751.
Molina-Infante et al. (May 7, 2008) "Overlap of Reflux and Eosinophilic Esophagitis in Two Patients Requiring Different Therapies: A Review of the Literature", World Journal of Gastroenterology, 14(9):1463-1466.
Mori et al. (Jan. 16, 2009) "Identification of the Human Eosinophil Lineage-committed Progenitor: Revision of Phenotypic Definition of the Human Common Myeloid Progenitor", Journal of Experimental Medicine, 206(1):183-193.
Mukhopadhyay et al. (Jul. 2010) "Matrix Metalloproteinase-12 is a Therapeutic Target for Asthma in Children and Young Adults", The Journal of Allergy and Clinical Immunology, 126(1):70-76.
Mulder et al. (Jan. 12, 2011) "Understanding Eosinophilic Esophagitis: The Cellular and Molecular Mechanisms of an Emerging Disease", Mucosal Immunology, 4(2):139-147.
Murata et al. (Jul. 2008) "Activation of Toll-like Receptor 2 by a Novel Preparation of Cell Wall Skeleton from Mycobacterium Bovis BCG Tokyo (SMP-105) Sufficiently Enhances Immune Responses Against Tumors", Cancer Science, 99(7):1435-1440.

Nagai et al. (Jun. 2006) "Toll-like Receptors on Hematopoietic Progenitor Cells Stimulate Innate Immune System Replenishment", Immunity, 24(6):801-812.
Nagase et al. (Oct. 15, 2003) "Expression and Function of Toll-like Receptors in Eosinophils: Activation by Toll-like Receptor 7 Ligand", Journal of Immunology, 171(8):3977-3982.
Navarro et al. (Jun. 1, 2010) "Small RNAs Guide Hematopoietic Cell Differentiation and Function", Journal of Immunology, 184(11):5939-5947.
Naya et al. (May 7, 2001) "Discovery of a Novel CCR3 Selective Antagonist", Bioorganic & Medicinal Chemistry Letters, 11(9):1219-1223.
Naya et al. (Jun. 2003) "Structure-Activity Relationships of 2-(Benzothiazolylthio)acetamide Class of CCR3 Selective Antagonist", Chemical and Pharmaceutical Bulletin, 51(6):697-701.
Newberry et al. (Nov. 2005) "Strongyloides Hyperinfection Presenting as Acute Respiratory Failure And Gram-negative Sepsis", Chest, 128(5):3681-3684.
Noel et al. (Jul. 2004) "Clinical and Immunopathologic Effects of Swallowed Fluticasone for Eosinophilic Esophagitis", Clinical Gastroenterology and Hepatology, 2(7):568-575.
Notterman et al. (2002) "Tumor Biology and Microarray Analysis of Solid Tumors: Colorectal Cancer as a Model System", Microarrays and Cancer Research, 81-111.
Novak et al. (Apr. 1, 2007) "CCL23 Expression is Induced by IL-4 in a STAT6-Dependent Fashion", Journal of Immunology, 178(7):4335-4341.
Ogbogu et al. (Dec. 2009) "Hypereosinophilic Syndromes: A Multicenter, Retrospective Analysis of Clinical Characteristics and Response to Therapy", The Journal of Allergy and Clinical Immunology, 124(6):1319-1325.
Ordoñez et al. (Dec. 2000) "Epithelial Desquamation in Asthma", American Journal of Respiratory and Critical Care Medicine, 162(6):2324-2329.
Ozawa et al. (Oct. 2009) "BRAK/CXCL14 Expression Oral Carcinoma Cells Completely Suppresses Tumor Cell Xenografts in SCID Mouse", Biomedical Research, 30(5):315-318.
Ozawa et al. (Oct. 11, 2009) "Restoration of BRAK/CXCL14 Gene Expression by Gefitinib is Associated with Antitumor Efficacy of the Drug in Head and Neck Squamous Cell Carcinoma", Cancer Science, 100(11):2202-2209.
Yousefi et al. 2008. Nature Medicine, 14(9):949-953.
Chen et al. Jiepoukexue Jinzhan (2007), 13(4), 388-391.
Chu et al. 2011. Nature Immuno, 12(2):151-159.
Elsner et al. 1997. Euro. J. of Immuno. vol. 27, pp. 2892-2898.
Sinicropi et al., BioMEMS and biomedical nanotechnology. Springer US, 2006. 23-46.
Lu et al., 2011. J. Immuno. pp. 3362-3373, vol. 187(16).
Sonkoly et al. 2010. J. of Aller and Clin. Immuno, 126(3):581-589.
Kalinin et al. Future Medicine, vol. 19, pp. 629-650, 2018.
Caldwell. J. Allergy. Clin. Immuno. 134:1114-24 (2014).
Eisen et al. 1998. Proc. Natl. Acad. Sci. USA (25)95, p. 14863-14868.
Shoda et al. Lancet. Gastroenterology Hepatol. Jul. 2018; 3(7):477-488; Epub 2018.
Sato et al. J. Allergy Clin. Immuno. Pract. 2017, 5(6):1639-1649.
Descamps et al., Cancer Res. 61, 4337-4340 (2001).
Madhusudan et al. Resent Results Cancer Res. 172:25-44.
Prakash et al. Expert Rev. Resp. Med. 4(3), 395-411 (2010).
Oyoshi Current Opinion in Pediatrics, 2015, 27(6), 741-747.
Rochlitzer et al. Biochem Soc. Trans (2006), 34(4), 594-599.
Nassenstein et al. J. Allergy Clin. Immuno. 2006; 118:597-605.
Weber et al. Experimental Dermatology, 2014. vol. 23, pp. 1-52.
Valeska et al. 2019. Gastroenterology. 156(6, Suppl. 1) S619. 1 page.
Wang et al. 1994. J. Immuno. 152(10):5014-5021.
European Search Report and Written Opinion for Application No. 12732079.4 Apr. 22, 2014, 11 pages.
Sato et al. (May 2011) "MicroRNAs and Epigenetics", The FEBS Journal, 278(10):1598-1609.
Sayed et al. (Jul. 2011) "MicroRNAs in Development and Disease", Physiological Reviews, 91(3):827-887.

(56) References Cited

OTHER PUBLICATIONS

Scherer et al. (2013) "Investigating the Speech Characteristics of Suicidal Adolescents", International Conference on Acoustics, Speech and Signal Processing, 5 pages.
Schmid-Grendelmeier et al. (Jul. 15, 2002) "Eosinophils Express Functional IL-13 in Eosinophilic Inflammatory Diseases", Journal of Immunology, 169(2):1021-1027.
Schoneberg et al. (Mar. 2, 2018) "Structural Basis of G Protein-coupled Receptor Function", Molecular and Cellular Endocrinology, 151(1-2):181-193.
Schultz et al. (May 26, 1998) "Smart, A Simple Modular Architecture Research Tool: Identification of Signaling Domains", Proceedings of the National Academy of Sciences of the United States of America, 95(11):5857-5864.
Sehmi et al. (Nov. 15, 1997) "Allergen-induced Increases in IL-5 Receptor Alpha-subunit Expression on Bone Marrow-derived CD34+ Cells from Asthmatic Subjects. A Novel Marker of Progenitor Cell Commitment Towards Eosinophilic Differentiation", Journal of Clinical Investigation, 100(10):2466-2475.
Sexton et al. (Sep. 2009) "Recent Advances in our Understanding of Peptide Hormone Receptors and Ramps", Current Opinion in Drug Discovery & Development, 2(5):440-448.
Shaaban et al. (Dec. 2010) "Eosinopenia: Is it a Good Marker of Sepsis in Comparison to Procalcitonin and C-reactive Protein Levels for Patients Admitted to a Critical Care Unit in an Urban Hospital?", Journal of Critical Care, 25(4):570-575.
Shah et al. (Mar. 2009) "Histopathologic Variability in Children with Eosinophilic Esophagitis", The American Journal of Gastroenterology, 104(3):716-721.
Sharma et al. (Aug. 5, 2011) "Protein Kinase R as Mediator of the Effects of Interferon (IFN) Gamma and Tumor Necrosis Factor (TNF) Alpha on Normal and Dysplastic Hematopoiesis", Journal of Biological Chemistry, 286 (31):27506-27514.
Shen et al. (Apr. 2011) "Plasma MicroRNAs as Potential Biomarkers for Non-small-cell Lung Cancer", Laboratory Investigation, 91(4):579-587.
Sheng et al. (Jun. 2011) "The MUC13 Cell Surface Mucin Protects Against Intestinal Inflammation by Inhibiting Epithelial Cell Apoptosis", Gut, 60(12):1661-1670.
Sherrill et al. (Jul. 2011) "Genetic Dissection of Eosinophilic Esophagitis Provides Insight into Disease Pathogenesis and Treatment Strategies", The Journal of Allergy and Clinical Immunology, 128(1):23-32.
Sherrill et al. (Jul. 1, 2010) "Variants of Thymic Stromal Lymphopoietin and its Receptor Associate with Eosinophilic Esophagitis", Journal of Allergy and Clinical Immunology, 126(1):160-165.
Shinkai et al. (Aug. 1, 1999) "A Novel Human CC Chemokine, Eotaxin-3, Which Is Expressed in IL-4-Stimulated Vascular Endothelial Cells, Exhibits Potent Activity Toward Eosinophils", The Journal of Immunology, 163 (3):1602-1610.
Shinkai et al. (Nov. 2002) "N-terminal Domain of Eotaxin-3 is Important for Activation of CC Chemokine Receptor 3", Protein Engineering, Design and Selection, 15(11):923-929.
Shoda et al. (Jan. 2020) "Molecular, Endoscopic, Histologic, and Circulating Biomarker-based Diagnosis of Eosinophilic Gastritis: Multi-site Study", The Journal of Allergy and Clinical Immunology, 145(1):255-269.
Zahm et al. (Jul. 2011) "Circulating MicroRNA is a Biomarker of Pediatric Crohn Disease", Journal of Pediatric Gastroenterology and Nutrition, 53(1):26-33.
Simon et al. (Oct. 10, 2005) "Roadmap for Developing and Validating Therapeutically Relevant Genomic Classifiers", Journal of Clinical Oncology, 23(29):7332-7341.
Simonini et al. (Nov. 15, 2010) "Epigenetically Deregulated Microrna-375 is Involved in a Positive Feedback Loop with Estrogen Receptor Alpha in Breast Cancer Cells", Cancer Research, 70(22):9175-9184.
Sin et al. (Sep. 2011) "Nerve Growth Factor or IL-3 Induces more IL-13 Production from Basophils of Allergic Subjects than from Basophils of Nonallergic Subjects", The Journal of Allergy and Clinical Immunology, 108 (3):387-393.
Yuan et al. (Feb. 7, 2011) "Microrna-203 Inhibits Cell Proliferation by Repressing Anp63 Expression in Human Esophageal Squamous Cell Carcinoma", BMC Cancer, 11:10 pages.
Slonim Donnak. (Dec. 2002) "From Patterns to Pathways: Gene Expression Data Analysis Comes of Age", Nature Genetics, 32:502-508.
Smith et al. (Jun. 2010) "Insulin-Like Growth Factor-I Regulation of Immune Function: A Potential Therapeutic Target in Autoimmune Diseases?", Pharmacological Reviews, 62(2):199-236.
Smith et al. (Feb. 7, 2010) "MicroRNAs, Development of Barrett's Esophagus, and Progression to Esophageal Adenocarcinoma", World Journal of Gastroenterology, 16(5):531-537.
Smith et al. (Dec. 2006) "Serine Proteases, their Inhibitors and Allergy", Allergy, 61(12):1441-1447.
Sonkoly et al. (Jul. 2007) "MicroRNAs: Novel Regulators Involved in the Pathogenesis of Psoriasis?", PLoS One, e610, 2(7):8 pages.
Sonkoly et al. (Dec. 2010) "MIR-155 is Overexpressed in Patients with Atopic Dermatitis and Modulates T-cell Proliferative Responses by Targeting Cytotoxic T Lymphocyte-associated Antigen 4", The Journal of Allergy and Clinical Immunology, 126(3):581-589.
Spergel et al. (Oct. 2005) "Treatment of Eosinophilic Esophagitis with Specific Food Elimination Diet Directed by a Combination of Skin Prick and Patch Tests", Annals of Allergy, Asthma & Immunology, 95(4):336-343.
Sprenger et al. (Jan. 2009) "Eosinophilic Oesophagitis: An Enigmatic, Emerging Disease", The Netherlands Journal of Medicine, 67(1):8-12.
Spry C. (Sep. 1976) "Eosinophilia in Addison's Disease", Yale Journal of Biology and Medicine, 49(4):411-413.
Stansfield et al. (Dec. 2009) "Periostin is a Novel Factor in Cardiac Remodeling After Experimental and Clinical Unloading of the Failing Heart", The Annals of Thoracic Surgery, 88(6):1916-1921.
Stappert et al. (Aug. 1994) "A Short Core Region of E-cadherin is Essential for Catenin Binding and is Highly Phosphorylated", Cell Communication & Adhesion, 2(4):319-327.
Stein et al. (Jun. 2008) "Anti-IL-5 (Mepolizumab) Therapy Reduces Eosinophil Activation Ex Vivo and Increases IL-5 and IL-5 Receptor Levels", The Journal of Allergy and Clinical Immunology, 121(6):1473-1483.
Stein et al. (Nov. 2010) "Targeting Interleukin (IL) 5 for Asthma and Hypereosinophilic Diseases", Recent Patents on Inflammation & Allergy Drug Discovery, 4(3):201-209.
Stothard P. (Jun. 2000) "Javascript Programs for Analyzing and Formatting Protein and DNA Sequences", BioTechniques, 28(6);1102, 1104.
Straumann et al. (Nov. 2010) "Budesonide is Effective in Adolescent and Adult Patients With Active Eosinophilic Esophagitis", Gastroenterology, 139(5):1526-1537.
Straumann et al. (Feb. 2005) "Eosinophilic esophagitis: escalating epidemiology?", The Journal of Allergy and Clinical Immunology, 115(2):418-419.
Straumann Alex (Feb. 3, 2012) "Eosinophilic Esophagitis: Rapidly Emerging Disorder", Swiss Medical Weekly, w13513, 142:8 pages.
Straumann et al. (Dec. 2001) "Idiopathic Eosinophilic Esophagitis is Associated with a T(H)2-type Allergic Inflammatory Response", The Journal of Allergy and Clinical Immunology, 108(6):954-961.
Straumann et al. (May 2011) "Long-term Budesonide Maintenance Treatment is Partially Effective for Patients with Eosinophilic Esophagitis", Clinical Gastroenterology and Hepatology, 9(5):370-372.
Straumann et al. (Apr. 2012) "Pediatric and Adult Eosinophilic Esophagitis: Similarities and Differences", Allergy, 67(4):477-490.
Strausberg et al. (2002) "Reading the Molecular Signatures of Cancer", Microarrays and Cancer Research, 11-16.
Suire et al. (Apr. 2005) "p84, a New Gβγ-activated Regulatory Subunit of the Type IB Phosphoinositide 3-kinase b110γ", Current Biology, 15(6):566-570.
Svensson et al. (Apr. 2005) "Human Eosinophils Selectively Recognize and Become Activated by Bacteria Belonging to Different Taxonomic Groups", Microbes and Infection, 7(4):720-728.

(56) References Cited

OTHER PUBLICATIONS

Talley et al. (Jan. 1990) "Eosinophilic Gastroenteritis: A Clinicopathological Study of Patients with Disease of the Mucosa, Muscle Layer, and Subserosal Tissues", Gut, 31(1):54-58.
Tan et al. (Mar. 15, 2011) "HYAL1 Overexpression is Correlated with the Malignant Behavior of Human Breast Cancer", International Journal of Cancer, 128(6):1303-1315.
Teitelbaum et al. (May 2002) "Eosinophilic Esophagitis in Children: Immunopathological Analysis and Response to Fluticasone Propionate", Gastroenterology, 122(5):1216-1225.
Tezza et al. (Jun. 2013) "Epigenetics of Allergy", Early Human Development, 89(Suppl 1):S20-S21.
Tian et al. (Oct. 1, 2010) "Visualizing of the Cellular Uptake and Intracellular Trafficking of Exosomes by Live-cell Microscopy", Journal of Cellular Biochemistry, 111(2):488-496.
Tkachuk et al. (Nov. 19, 1996) "Regulation and Role of Urokinase Plasminogen Activator in Vascular Remodelling", Clinical and Experimental Pharmacology and Physiology, 23(9):759-765.
Todorov et al. (2018) "Principal Components Analysis: Theory and Applicaiton to Gene Expression Data Analysis", Genomics and Computational Biology, e100041, 4(2):7 pages.
Trapnell et al. (Apr. 2009) "TopHat: Discovering Splice Junctions with RNA-Seq", Bioinformatics, 25(9):1105-1111.
Trapnell et al. (May 2010) "Transcript Assembly and Quantification By RNA-seq Reveals Unannotated Transcripts and Isoform Switching During Cell Differentiation", Nature Biotechnology, 28(5):511-515.
Tsang et al. (Mar. 2010) "Oncofetal H19-derived MIR-675 Regulates Tumor Suppressor RB in Human Colorectal Cance", Carcinogenesis, 31(3):350-358.
Tsuchiya et al. (Jan. 7, 2011) "MicroRNA-210 Regulates Cancer Cell Proliferation through Targeting Fibroblast Growth Factor Receptor-like 1 (FGFRLI)", Journal of Biological Chemistry, 286(1):420-428.
Tsukamoto et al. (Mar. 15, 2010) "MicroRNA-375 is Downregulated in Gastric Carcinomas and Regulates Cell Survival by Targeting PDK1 and 14-3-3ζ", Cancer Research, 70(6):2339-2349.
Tzvetkov et al. (Jul. 5, 2013) "Morphine is a substrate of the organic cation transporter OCT1 and polymorphisms in OCT1 gene affect morphine pharmacokinetics after codeine administration", Biochemical Pharmacology, 86(5):666-678.
Ueda et al. (Jun. 6, 2005) "Inflammation and the Reciprocal Production of Granulocytes and Lymphocytes in Bone Marrow", Journal of Experimental Medicine, 201(11):1771-1780.
Vaishnavi et al. (2013) "Oncogenic and Drug-Sensitive NTRK1 Rearrangements in Lung Cancer", Nature Medicine, 19(11):1469-1472.
Valadi et al. (Jun. 2007) "Exosome-Mediated Transfer of mRNA and microRNA is a Novel Mechanism of Genetic Exchange Between Cells", Nature Cell Biology, 9(6):654-659.
Van Rooij et al. (Feb. 3, 2012) "Developing microRNA Therapeutics", Circulation Research, 110(3):496-507.
Vandepapeliere et al. (Jan. 14, 2008) "Vaccine Adjuvant Systems Containing Monophosphoryl Lipid A and QS21 Induce Strong C63 and Persistent Humoral and T Cell Responses Against Hepatitis B Surface Antigen in Healthy Adult Volunteers", Vaccine, 33(8):1084-1091.
Varnes et al. (Apr. 5, 2004) "Discovery of N-propylurea 3-benzylpiperidines as Selective CC Chemokine Receptor-3 (CCR3) Antagonists", Bioorganic & Medicinal Chemistry Letters, 14(7):1645-1649.
Velasco et al. (Mar. 2005) "Toll-like Receptor 4 or 2 Agonists Decrease Allergic Inflammation", American Journal of Respiratory Cell and Molecular Biology, 32(3):218-224.
Velu et al. (May 7, 2009) "Gfi1 Regulates miR-21 and miR-196b to Control Myelopoiesis", Blood, 113(19):4720-4728.
Venek et al. (2014) "Adolescent Suicidal Risk Assessment in Clinician-Patient Interaction: A Study of Verbal and Acoustic Behaviors", Spoken Language Technology Workshop, 6 pages.
Venge Per (May 2010) "The Eosinophil and Airway Remodelling in Asthma", The Clinical Respiratory Journal, 4 (Suppl 1):15-19.
Venkatasubramanian et al. (Jul. 2014) "ABCC3 and OCT1 genotypes influence pharmacokinetics of morphine in children", Pharmacogenomics, 15(10):1297-1309.
Verspoor et al. (Jun. 15, 2009) "The textual characteristics of traditional and Open Access scientific journals are similar", BMC Bioinformatics, 10:183.
Vicario et al. (Jan. 2010) "Local B Cells and IgE Production in the Oesophageal Mucosa in Eosinophilic Oesophagitis", Gut, 59(1):12-20.
Vincent et al. (Dec. 2, 2009) "International Study of the Prevalence and Outcomes of Infection in Intensive Care Units", JAMA 302(21):2323-2329.
Von Ahlfen et al. (2007) "Determinants of RNA Quality from FFPE Samples", PLoS One, e1261, 2(12): 7 pages.
Von Arnim et al. (2014) "Eosinophilic Esophagitis—Treatment of Eosinophilic Esophagitis with Drugs: Corticosteroids", Digestive Diseases, 32(1-2):126-129.
Wacker et al. (Jul. 8, 2002) "CCR3 Antagonists: A Potential New Therapy for the Treatment of Asthma. Discovery and Structure-activity Relationships", Bioorganic & Medicinal Chemistry Letters, 12(13):1785-1789.
Wan et al. (Feb. 2004) "Foxa2 Regulates Alveolarization and Goblet Cell Hyperplasia", Development, 131(4):953-964.
Wang et al. (May 2010) "Differential Functions of Growth Factor Receptor-Bound Protein 7 (GRB7) and Its Variant GRB7v in Ovarian Carcinogenesis", Clinical Cancer Research, 16(9):2529-2539.
Yousefi et al. (Aug. 10, 2008) "Catapult-like Release of Mitochondrial DNA by Eosinophils Contributes to Antibacterial Defense", Nature Medicine, 14(9):949-953.
Wen et al. (Oct. 19, 2014) "Transcriptome analysis of proton pump inhibitor-responsive esophageal eosinophilia reveals proton pump inhibitor-reversible allergic inflammation", Journal of Allergy and Clinical Immunology, 135(1):187-197.
White (Nov. 24, 2000) "Identification of Potent, Selective Nonpeptide CC Chemokine Receptor-3 Antagonist that Inhibits Eotaxin-, Eotaxin-2-, and Monocyte Chemotactic Protein-4-induced Eosinophil Migration", The Journal of Biological Chemistry, 275(47):36626-36631.
Wills-Karp Marsha (Dec. 2004) "Interleukin-13 in Asthma Pathogenesis", Immunological Reviews, 202:175-190.
Winter et al. (Mar. 2009) "Many Roads to Maturity: microRNA Biogenesis Pathways and their Regulation", Nature Cell Biology, 11(3):228-234.
Wolska et al. (Apr. 2009) "The Role of Toll-Like Receptors in Hematopoietic Malignancies", Current Molecular Medicine, 9(3):324-335.
Wong et al. (Jul. 2007) "Intracellular Signaling Mechanisms Regulating Toll-like Receptor-mediated Activation of Eosinophils", American Journal of Respiratory Cell and Molecular Biology, 37(1):85-96.
Wong et al. (Feb. 2013) "Microrna-21 Regulates the Prosurvival Effect of GM-CSF on Human Eosinophils", Immunobiology, 218(2):255-262.
Woodruff et al. (Oct. 2, 2007) "Genome-wide Profiling Identifies Epithelial Cell Genes Associated with Asthma and With Treatment Response to Corticosteroids", Proceedings of the National Academy of Sciences of the United States of America, 10(40):15858-15863.
Wu et al. (Nov. 2008) "MicroRNAs are Differentially Expressed in Ulcerative Colitis and Alter Expression of Macrophage Inflammatory Peptide-2α", Gastroenterology, e24, 135(5):1624-1635.
Xanthou Marietta (Sep. 2008) "Leucocyte Blood Picture in Ill Newborn Babies", Archives of Disease in Childhood, 47(255):741-746.
Xiang et al. (Feb. 15, 2008) "Wound Repair and Proliferation of Bronchial Epithelial Cells Regulated by CTNNAL 1", Journal of Cellular Biochemistry, 103(3):920-930.
Xing et al. (Aug. 23, 2011) "Protease Phenotype of Constitutive Connective Tissue and of Induced Mucosal Mast Cells in Mice is Regulated by the Tissue", Proceedings of the National Academy of Sciences of the United States of America, 108(34):4210-1421.

(56) References Cited

OTHER PUBLICATIONS

Yamazaki et al. (Nov. 2006) "Allergen-specific In Vitro Cytokine Production in Adult Patients with Eosinophilic Esophagitis", Digestive Diseases and Sciences, 51(11):1934-1941.
Yang et al. (Oct. 15, 2006) "Inhibition of Arginase I Activity by RNA Interference Attenuates IL-13-Induced Airways Hyperresponsiveness", The Journal of Immunology, 177(8):5595-5603.
Yang et al. (May 2009) "Th17 and Natural Treg Cell Population Dynamics in Systemic Lupus Erythematosus", Arthritis & Rheumatology, 60(5);1472-1483.
Yee et al. (Jul. 3, 2012) "Insulin-like Growth Factor Receptor Inhibitors: Baby or the Bathwater?", Journal of the National Cancer Institute, 104(13):975-981.
Yi et al. (Mar. 13, 2008) "A Skin MicroRNA Promotes Differentiation by Repressing 'Stemness'", Nature, 452(7184):225-229.
Yin et al. (Jan. 2010) "Targeting the Insulin-like Growth Factor-1 Receptor by Picropodophyllin as a Treatment Option for Glioblastoma", Neuro-Oncology, 12(1):19-27.
European Search Report for Application No. 19787916.6, dated Mar. 1, 2022 (nine (9) pages.
Ferguson et al., "Pediatric Eosinophilic Esophagitis Endotypes: Are we closer to predicting treatment response?" Clin Rev Allergy Immunol 55(1):43-55 (2018). doi:10.1007/s12016-017-8658-8.
Ochiai et al., "Thymic stromal lymphopoietin drives the development of IL-13+ Th2 cells", Proceedings of the National Academy of Sciences115(5):1033-1038 (2018).
Butz et al., "Efficacy, Dose Reduction, and Resistance to High-Dose Fluticasone in Patients With Eosinophilic Esophagitis" Gastroenterology 2014; 147:324-333.
Siddique et al., "Clinicopathologic and gene expression analysis of initial biopsies from patients with eosinophilic esophagitis refractory to therapy" Human Pathology (2017) 68, 79-86.
Kalinin et al., "Deep learning in pharmacogenomics: from gene regulation to patient stratification" Pharmacogenomics (2018) 19(7), 629-650.
Azouz, et al. (May 27, 2020) Supplemental Materials for Functional Role of Kallikrein 5 and Proteinase-activated 9 Receptor 2 in Eosinophilic Esophagitis, Sci. Transl. Med. 12 eaaz773, sciencemag. org/cgi/contenVfull/12/545, 26 pgs.
Fulkerson et al. (Oct. 31, 2006) "A Central Regulatory Role for Eosinophils and the Eotaxin/CCR3 Axis in Chronic Experimental Allergic Airway Inflammation", Proceedings of the National Academy of Sciences of the United States of America, 103(44):16418-16423.
Fulkerson et al. (Feb. 2013) "Targeting Eosinophils in Allergy, Inflammation and Beyond", Nature Reviews Drug Discovery, 12(2):117-129.
Furuta et al. (Oct. 2007) "Eosinophilic Esophagitis in Children and Adults: A Systematic Review and Consensus Recommendations for Diagnosis and Treatment", Gastroenterology, 133(4):1342-1363.
Garbacki et al. (Jan. 28, 2011) "MicroRNAs Profiling in Murine Models of Acute and Chronic Asthma: A Relationship with mRNAs Targets", PLoS One, e16509, 6(1):23 pages.
Garcia-Echeverria et al. (Apr. 2004) "In Vivo Antitumor Activity of NVP-AEW541-A Novel, Potent, and Selective Inhibitor of the IGF-IR Kinase", Cancer Cell, 5(3):231-239.
Garçon et al. (Aug. 1, 2011) "Development of an AS04-adjuvanted HPV Vaccine with the Adjuvant System Approach", BioDrugs, 25(4):217-226.
Garrett et al. (Jan. 2004) "Anti-interleukin-5 (Mepolizumab) Therapy for Hypereosinophilic Syndrome", Journal of Allergy and Clinical Immunology, 113(1):115-119.
Zimmerman et al. (Feb. 2003) "Chemokines in Asthma: Cooperative Interaction between Chemokines and IL-13", The Journal of Allergy and Clinical Immunology, 111(2):227-242.
Zheng et al. (Mar. 2009) "Transgenic Expression of Interleukin-13 in the Skin Induces a Pruritic Dermatitis and Skin Remodeling", Journal of Investigative Dermatology, 129(3):742-751.

Zhen et al. (Feb. 2007) "IL-13 and Epidermal Growth Factor Receptor Have Critical but Distinct Roles in Epithelial Cell Mucin Production", American Journal of Respiratory Cell and Molecular Biology, 36(2):244-253.
Georgantas et al. (Feb. 20, 2007) "CD34+ Hematopoietic Stem-progenitor Cell MicroRNA Expression and Function: A Circuit Diagram of Differentiation Control", Proceedings of the National Academy of Sciences of the United States of America, 104(8):2750-2755.
Gilbert et al. (Aug. 1978) "Effects of Acute Endotoxemia and Glucose Administration on Circulating Leukocyte Populations in Normal and Diabetic Subjects", Metabolism, 27(8):889-899.
Goettig et al. (2010) "Natural and Synthetic Inhibitors of Kallikrein-Related Peptidases (KLKs)", Biochimie, 92(11):1546-67.
Gong et al. (May 30, 2013) "Gene polymorphisms of OPRM1 A118G and ABCB1 C3435T may influence opioid requirements in Chinese patients with cancer pain", Asian Pacific Journal of Cancer Prevention, 14(5):2937-2943.
Gonsalves et al. (Jan. 2020) "Diagnosis and Treatment of Eosinophilic Esophagitis", The Journal of Allergy and Clinical Immunology, 145(1):1-7.
Gonsalves et al. (Sep. 2006) "Histopathologic Variability and Endoscopic Correlates in Adults with Eosinophilic Esophagitis", Gastrointestinal Endoscopy, 64(3):313-319.
Griffiths-Jones et al. (2006) "miRBase: MicroRNA Sequences, Targets and Gene Nomenclature", Nucleic Acids Research, 34:D140-D144.
Griffiths-Jones et al. (Jan. 2008) "miRBase: Tools for Micro RNA Genomics", Nucleic Acids Research, 36 (Database issue):D154-D158.
Gupta et al. (Jan. 2006) "Cytokine Expression in Normal and Inflamed Esophageal Mucosa: A Study into the Pathogenesis of Allergic Eosinophilic Esophagitis", Journal of Pediatric Gastroenterology and Nutrition: , 42(1):22-26.
Gupta et al. (May 1998) "Expression of Inducible Nitric Oxide Synthase (iNOS) mRNA in Inflamed Esophageal and Colonic Mucosa in a Pediatric Population", American Journal of Gastroenterology, 93(5):795-798.
Guyon et al. (Jan. 2002) "Gene Selection for Cancer Classification using Support Vector Machines", Machine Learning, 46:389-422.
Hahn et al. (Apr. 2006) "Airway Epithelial Cells Produce Neurotrophins and Promote the Survival of Eosinophils During Allergic Airway Inflammation", Journal of Allergy and Clinical Immunology, 117(4):787-794.
Hamilton et al. (1980) "Regulation of The Plasminogen Activator Activity of Macrophage Tumor Cell Lines", International Journal of Immunopharmacology, 2(4):353-362.
Hamoui et al. (Aug. 2004) "Increased Acid Exposure in Patients With Gastroesophageal Reflux Disease Influences Cyclooxygenase-2 Gene Expression in the Squamous Epithelium of the Lower Esophagus", Archives of Surgery, 139 (7):712-716.
Hardiman Gary (Nov. 5, 2004) "Microarray Platforms—Comparisons and Contrasts", Pharmacogenomics, 5 (5):487-502.
Hatley et al. (Sep. 14, 2010) "Modulation of K-Ras-dependent Lung Tumorigenesis by MicroRNA-21", Cancer Cell, 18(3):282-293.
Heib et al. (May 2019) "Wheat Amylase/Trypsin Inhibitors Aggravate Eosinophilic Esophagitis", Gastroenterology, 6 (Suppl. 1):1 page.
Hennessy et al. (Apr. 2010) "Targeting Toll-Like Receptors: Emerging Therapeutics?", Nature Reviews Drug Discovery, 9(4):293-307.
Himes et al. (Mar. 4, 2009) "Prediction of Chronic Obstructive Pulmonary Disease (COPD) in Asthma Patients Using Electronic Medical Records", Journal of the American Medical Informatics Association, 16(3):371-379.
Hogan et al. (May 2008) "Eosinophils: Biological Properties and Role in Health and Disease", Clinical & Experimental Allergy, 38(5):709-750.
Hogan et al. (Dec. 2004) "The Eosinophil as a Therapeutic Target in Gastrointestinal Disease", Alimentary Pharmacology and Therapeutics, 20(11-12):1231-1240.
Hotchkiss et al. (Jun. 1, 2001) "Sepsis-induced Apoptosis Causes Progressive Profound Depletion of B and CD4+ T Lymphocytes in Humans", Journal of Immunology, 166(11):6952-6963.

(56) References Cited

OTHER PUBLICATIONS

Huang et al. (Jul. 1, 2006) "RegRNA: An Integrated Web Server for Identifying Regulatory RNA Motifs and Elements", Nucleic Acids Research, 34:W429-W434.
Hwang et al. (Apr. 30, 2005) "Expression of IL-17 Homologs and their Receptors in the Synovial Cells of Rheumatoid Arthritis Patients", Molecular Cell, 19(2):180-184.
Indo Y. (Dec. 2001) "Molecular Basis of Congenital Insensitivity to Pain with Anhidrosis (CIPA): Mutations and Polymorphisms in TRKA (NTRK1) Gene Encoding the Receptor Tyrosine Kinase for Nerve Qrowth Factor", Human Mutation, 18(6):462-471.
Indo et al. (Aug. 1996) "Mutations in the TRKA/NGF Receptor Gene in Patients with Congenital Insensitivity to Pain with Anhidrosis", Nature Genetics, 13(4):485-488.
Indo Y. (Oct. 2012) "Nerve Growth Factor and the Physiology of Pain: Lessons from Congenital Insensitivity to Pain with Anhidrosis", Clinical Genetics, 82(4):341-350.
IP et al. (Dec. 2007) "Interleukin-31 Induces Cytokine and Chemokine Production from Human Bronchial Epithelial Cells through Activation of Mitogen-activated Protein Kinase Signalling Pathways: Implications for the Allergic Response", Immunology, 122(4):532-541.
Iwasaki et al. (Jun. 20, 2005) "Identification of Eosinophil Lineage-committed Progenitors in the Murine Bone Marrow", Journal of Experimental Medicine, 201(12):1891-1897.
Jacobsen et al. (Jun. 2007) "Eosinophils: Singularly Destructive Effector Cells or Purveyors of Immunoregulation?", The Journal of Allergy and Clinical Immunology, 119(6):1313-1320.
Jakiela et al. (Oct. 2009) "Intrinsic Pathway of Apoptosis in Peripheral Blood Eosinophils of Churg-strauss Syndrome", Rheumatology (Oxford), 48(10):1202-1207.
Jia et al. (Nov. 2008) "Mist1 Regulates Pancreatic Acinar Cell Proliferation through p21 CIP1/WAF1", Gastroenterology, 135(5):1687-1697.
Jiang et al. (Jul. 2011) "The Emerging Role of MicroRNAs in Asthma", Molecular and Cellular Biochemistry, 353(1-2):35-40.
Johnnidis et al. (Feb. 28, 2008) "Regulation of Progenitor Cell Proliferation and Granulocyte Function by MicroRNA-223", Nature, 451:1125-1129.
Juffali et al. (2010) "The WiNAM project: Neural data analysis with applications to epilespy", Biomedical Circuits and Systems Conference, 45-48.
Junttila et al. (Oct. 27, 2008) "Tuning Sensitivity to IL-4 and IL-13: Differential Expression of IL-4Ralpha, L-13Ralpha1, and Gammac Regulates Relative Cytokine Sensitivity", Journal of Experimental Medicine, 205 (11):2595-2608.
Kaiko et al. (Feb. 2011) "New Insights into the Generation of Th2 Immunity and Potential Therapeutic Targets for the Treatment of Asthma", Current Opinion in Allergy and Clinical Immunology, 11(1):39-45.
Kaimal et al. (Jul. 2010) "Toppcluster: A Multiple Gene List Feature Analyzer for Comparative Enrichment Clustering and Network-based Dissection of Biological System", Nucleic Acids Research, 38:W96-W102.
Kanzler et al. (May 3, 2007) "Therapeutic Targeting of Innate Immunity with Toll-like Receptor Agonists and Antagonists", Nature Medicine, 13(5):552-559.
Kariyawasam et al. (Sep. 2009) "Activin and Transforming Growth Factor-β Signaling Pathways are Activated after Allergen Challenge in Mild Asthma", The Journal of Allergy and Clinical Immunology, 124(3):454-462.
Ozdas et al. (Sep. 2004) "Investigation of Vocal Jitter and Glottal Flow Spectrum as Possible Cues for Depression and Near-Term Suicidal Risk", Transactions on Biomedical Engineering, 51(9):1530-1540.
Papagiannakopoulos et al. (Oct. 1, 2008) "MicroRNA-21 Targets a Network of Key Tumor-Suppressive Pathways in Glioblastoma Cells", Cancer Research, 68(19):8164-8172.
Park et al. (Dec. 27, 2006) "Genetic polymorphisms in the ABCB1 gene and the effects of fentanyl in Koreans", Clinical Pharmacology & Therapeutics, 81(4):539-546.
Patent Cooperation Treaty, "International Preliminary Report on Patentability and Written Opinion in corresponding International application No. PCT/US2012/044061", mailed on Dec. 23, 2013, 7 pages.
PCTUS2015044461,"International Search Report mailed on Nov. 9, 2015 for International Application No. PCT/US2015/044461", 11 pages.
Peeters et al. (Apr. 8, 2005) "Real-time RT-PCR Quantification of mRNA Encoding Cytokines and Chemokines in Histologically Normal Canine Nasal, Bronchial and Pulmonary Tissue", Veterinary Immunology and Immunopathology, 104(3-4):195-204.
Persson et al. (Jun. 2001) "Bactericidal Activity of Human Eosinophilic Granulocytes Against *Escherichia coli*", Infection and Immunity, 69(6):3591-3596.
Petriv et al. (Aug. 31, 2010) "Comprehensive MicroRNA Expression Profiling of the Hematopoietic Hierarchy", Proceedings of the National Academy of Sciences of the United States of America, 107(35):15443-15448.
Phipps et al. (Sep. 1, 2007) "Eosinophils Contribute to Innate Antiviral Immunity and Promote Clearance of Respiratory Syncytial Virus", Blood, 110(5):1578-1586.
Plötz et al. (Jan. 1, 2001) "The Interaction of Human Peripheral Blood Eosinophils with Bacterial Lipopolysaccharide is CD14 Dependent", Blood, 97(1):235-241.
Polikepahad et al. (Sep. 24, 2010) "Proinflammatory Role for let-7 MicroRNAs in Experimental Asthma", Journal of Biological Chemistry, 285(39):30139-30149.
Pouladi et al. (Jan. 2004) "Interleukin-13-dependent Expression of Matrix Metalloproteinase-12 is Required for the Development of Airway Eosinophilia in Mice", American Journal of Respiratory Cell and Molecular Biology, 30(1):84-90.
Proudfoot et al. (Nov. 5, 1999) "Amino-terminally Modified Rantes Analogues Demonstrate Differential Effects on Rantes Receptors", Journal of Biological Chemistry, 274(45):32478-32485.
Prows et al. (Nov. 13, 2013) "Codeine-related adverse drug reactions in children following tonsillectomy: a prospective study", Laryngoscope, 124(5):1242-1250.
Prussin et al. (Dec. 2009) "Eosinophilic Gastrointestinal Disease and Peanut Allergy are Alternatively Associated with IL-5+ and IL-5(-) T(H)2 Responses", The Journal of Allergy and Clinical Immunology, 124(6):1326-1332.
Zeng et al. (Feb. 2006) "Extracting Principal Diagnosis, Co-morbidity and Smoking Status for Asthma Research: Evaluation of a Natural Language Processing System", BMC Medical Informatics and Decision Making, 6(1):9 pages.
Zediak et al. (Mar. 1, 2011) "Cutting Edge: Persistently Open Chromatin at Effector Gene Loci in Resting Memory CD8+ T Cells Independent of Transcriptional Status", Journal of Immunology, 186(5):2705-2709.
Raap et al. (Feb. 2010) "The Role of Neurotrophins in the Pathophysiology of Allergic Rhinitis", Current Opinion in Allergy and Clinical Immunology, 10(1):8-13.
Rabinowits et al. (Jan. 2009) "Exosomal microRNA: a Diagnostic Marker for Lung Cancer", Clinical Lung Cancer, 10(1):42-46.
Rahaghi et al. ( 2017) "Long-term Clinical Outcomes Following Treatment with Alpha 1-Proteinase Inhibitor for COPD associated with alpha-1 Antitrypsin Deficiency: A Look at the Evidence", Respiratory Researc, 18(1):9 Pages.
Wechsler et al. (Jul. 2018) "Esophagitis Reference Score Accurately Identifies Disease Activity and Treatment Effects in Children", Clinical Gastroenterology and Hepatology, 16(7):1056-1063.
Ramirez et al. (Dec. 15, 2004) "Immortalization of Human Bronchial Epithelial Cells in the Absence of Viral Oncoproteins", Cancer Research, 64(24):9027-9034.
Ramirez et al. (Aug. 2006) "Transcriptional Regulation of the Human α2(I) Collagen Gene (COL1A2), an Informative Model System to Study Fibrotic Diseases", Matrix Biology, 25(6):365-372.
Rank et al. (May 2020) "Technical Review on the Management of Eosinophilic Esophagitis: A Report from the AGA Institute and the

(56) References Cited

OTHER PUBLICATIONS

Joint Task Force on Allergy-immunology Practice Parameters", Annals of Allergy, Asthma & Immunology, e17, 124(5):424-440.
Ray et al. (May 16, 2011) "Human Mu Opioid Receptor (OPRM1 A 118G) polymorphism is associated with brain mu-opioid receptor binding potential in smokers", PNAS, 108(22):9268-9273.
Raychaudhuri et al. (2000) "Principal Components Analysis to Summarize Microarray Experiments: Application to Sporulation Time Series", Pacific Symposium on Biocomputing, 5:452-463.
Robinson et al. (Jan. 1999) "CD34(+)/Interleukin-5Ralpha Messenger RNA+ Cells in the Bronchial Mucosa in Asthma: Potential Airway Eosinophil Progenitors", American Journal of Respiratory Cell and Molecular Biology, 20(1):9-13.
Collins et al. (Mar. 2017) "Newly Developed and Validated Eosinophilic Esophagitis Histology Scoring System and Evidence that it Outperforms Peak Eosinophil Count for Disease Diagnosis and Monitoring", Diseases of the Esophagus, 30(3):1-8.
Rochman et al. (Jul. 2015) "Neurotrophic Tyrosine Kinase Receptor 1 is a Direct Transcriptional and Epigenetic Target of IL-13 Involved in Allergic Inflammation", Immunology, 8(4):785-798.
Rodrigo et al. (Feb. 2008) "High Intraepithelial Eosinophil Counts in Esophageal Squamous Epithelium are Not Specific for Eosinophilic Esophagitis in Adults", The American Journal of Gastroenterology, 103(2);435-442.
Romani et al. (Jul. 9, 2002) "Cluster Analysis of Gene Expression Dynamics", Proceedings of the National Academy of Sciences, 99(14):9121-9126.
Rosas et al. (Jul. 2006) "IL-5-mediated Eosinophil Survival Requires Inhibition of GSK-3 and Correlates with β-catenin Relocalization", Journal of Leukocyte Biology, 80(1):186-195.
Rothenberg Marc E. (Oct. 2009) "Biology and Treatment of Eosinophilic Esophagitis", Gastroenterology, 137(4):1238-1249.
Rothenberg et al. (Apr. 2010) "Common Variants at 5q22 Associate with Pediatric Eosinophilic Esophagitis", Nature Genetics, 42(4):289-291.
Rothenberg et al. (Jan. 2004) "Eosinophilic Gastrointestinal Disorders (EGID)", The Journal of Allergy and Clinical ImmunologyThe Journal of Allergy and Clinical Immunology, 113(1):11-28.
Rothenberg et al. (Dec. 2001) "Pathogenesis and Clinical Features of Eosinophilic Esophagitis", The Journal of Allergy and Clinical Immunology, 108(6):891-894.
Rothenberg et al. (Apr. 2010) "The Eosinophil", Annual Review of Immunology, 24:147-174.
Rothenberg et al. (Mar. 20, 2008) "Treatment of Patients with the Hypereosinophilic Syndrome with Mepolizumab", The New England Journal of Medicine, 358(12):1215-1228.
Russ et al. (2013) "T Cell Immunity as a Tool for Studying Epigenetic Regulation of Cellular Differentiation", Frontiers in Genetics, 4:218.
Sabroe et al. (Aug. 25, 2000) "A Small Molecule Antagonist of Chemokine Receptors CCR1 and CCR3", The Journal of Biological Chemistry, 275(34):25985-25992.
Sabroe et al. (May 1, 2002) "Toll-Like Receptor (TLR)2 and TLR4 in Human Peripheral Blood Granulocytes: A Critical Role for Monocytes in Leukocyte Lipopolysaccharide Responses", The Journal of Immunology, 168(9):4701-4710.
Sadhasivam et al. (2014) "Genetics of pain perception, COMT and postoperative pain management in children", The Pharmacogenomics Journal, 15(3):277-284.
Sadhasivam et al. (Jul.-Aug. 2012) "Morphine clearance in children: does race or genetics matter?", Journal of Opioid Management, 8(4):217-226.
Sadhasivam et al. (2015) "Novel Associations between FAAH Genetic Varients an Postoperative Central Opioid Related Adverse Effects", The Pharmacogenomics Journal, 15(5):436-442.
Sadhasivam et al. (Jun. 13, 2012) "Preventing Opioid-Related Deaths in Children Undergoing Surgery", Pain Medicine, 13(7):982-983.
Sadhasivam et al. (Apr. 23, 2012) "Race and unequal burden of perioperative pain and opioid related adverse effects in children", Pediatrics, 129(5):832-838.
Saeki et al. (Mar. 2, 2001) "Identification of a Potent and Nonpeptidyl CCR3 Antagonist", Biochemical and Biophysical Research Communications, 281(3):779-782.
Sahin et al. (Oct. 2014) "mRNA-Based Therapeutics—Developing a New Class of Drugs", Nature reviews, 13(10):759-780.
Saini et al. (Nov. 27, 2008) "Annotation of Mammalian Primary microRNAs", BMC Genomics, Article No. 564, 9(1):19 pages.
Saito et al. (Mar. 15, 2002) "Pathogenesis of Murine Experimental Allergic Rhinitis: A Study of Local and Systemic Consequences of IL-5 Deficiency", The Journal of Immunology, 168(6):3017-3023.
Assa'ad et al. (Nov. 2011) "An Antibody Against IL-5 Reduces Numbers of Esophageal Intraepithelial Eosinophils in Children With Eosinophilic Esophagitis", Gastroenterology, 141(5):1593-1604.
Assa'ad et al. (Mar. 2007) "Pediatric Patients With Eosinophilic Esophagitis: An 8-year Follow-up", The Journal of Allergy and Clinical Immunology, 119(3):731-738.
Attwood et al. (Jan. 1993) "Esophageal Eosinophilia with Dysphagia. A Distinct Clinicopathologic Syndrome", Digestive Diseases and Sciences, 38(1):109-116.
Aune et al. (Mar. 2009) "Epigenetics and T helper 1 Differentiation", Immunology, 126(3):299-305.
Ayala et al. (May 15, 1996) "Differential Induction of Apoptosis in Lymphoid Tissues during Sepsis: Variation in Onset, Frequency, and the Nature of the Mediators", Blood, 87(10):4261-4275.
Azouz et al. (May 27, 2020) "Functional Role of Kallikrein 5 and Proteinase-activated Receptor 2 in Eosinophilic Esophagitis", Science Translational Medicine, eaaz7773, 12(545):34 pages.
Azouz et al. (Feb. 2016) "Loss of SPINK7 in Esophageal Epithelial Cells Unleashes a Pro-Inflammatory Response Characterized by Excessive Cytokine Production and Loss of Barrier Function", The Journal of Allergy and Clinical Immunology, 137(2):1 page.
Azouz et al. (Jun. 6, 2818) "The Antiprotease SPINK7 Serves as an Inhibitory Checkpoint for Esophageal Epithelial Inflammatory Responses", Science Translational Medicine, 10(444):29 pages.
Baker et al. (Apr. 2, 2003) "The Central Role of Receiver Operating Characteristic (ROC) Curves in Evaluating Tests for the Early Detection of Cancer", Journal of the National Cancer Institute, 95(7):511-515.
Baldrick et al. (Jul.-Aug. 2007) "Pollinex Quattro Ragweed: Safety Evaluation of a New Allergy Vaccine Adjuvanted with Monophosphoryl Lipid a (MPL) for the Treatment of Ragweed Pollen Allergy", Journal of Applied Toxicology, 27(4):399-409.
Barratt et al. (Apr. 18, 2012) "ABCB1 haplotype and OPRM1 118A > G genotype interaction in methadone maintenance treatment pharmacogenetics", 5(1):53-62.
Barski et al. (Oct. 2009) "Chromatin Poises miRNA- and Protein-coding Genes for Expression", Genome Research, 19(10):1742-151.
Bass D.A. (Jun. 1975) "Behavior of Eosinophil Leukocytes in Acute Inflammation. I. Lack of Dependence on Adrenal Function", Journal of Clinical Investigation, 55(6):1229-1236.
Bass D.A. (Oct. 1975) "Behavior of Eosinophil Leukocytes in Acute Inflammation II. Eosinophil Dynamics During Acute Inflammation", Journal of Clinical Investigation, 56(4):870-879.
Ben-Dor et al. (2000) "Tissue Classification with Gene Expression Profiles", Journal of Computational Biology, 7(3-4):559-583.
Berkman et al. (Jun. 2001) "Eotaxin-3 but Not Eotaxin Gene Expression is Upregulated in Asthmatics 24 Hours after Allergen Challenge", American Journal of Respiratory Cell and Molecular Biology, 24(6):682-687.
Bhattacharya et al. (Dec. 2007) "Increased Expression of Eotaxin-3 Distinguishes Between Eosinophilic Esophagitis and Gastroesophageal Reflux Disease", Human Pathology, 38(12):1744-1753.
Biesiada et al. (Nov. 2014) "Genetic risk signatures of opioid-induced respiratory depression following pediatric tonsillectomy", Pharmacogenomics, 15(14):1749-1762.
Biton et al. (Mar. 2011) "Epithelial MicroRNAs Regulate Gut Mucosal Immunity via Epithelium-T Cell Crosstalk", Nature Immunology, 12(3):239-246.

(56) References Cited

OTHER PUBLICATIONS

Blanchard et al. (Jan. 2011) "A Striking Local Esophageal Cytokine Expression Profile in Eosinophilic Esophagitis", The Journal of Allergy and Clinical Immunology, e7, 127(1):208-217.
Blanchard et al. (Jan. 2008) "Basics Pathogenesis of Eosinophilic Esophagitis", Gastrointestinal Endoscopy Clinics of North America, 18(1):133-143.
Blanchard et al. (Apr. 1, 2010) "Coordinate Interaction Between IL-13 and Epithelial Differentiation Cluster Genes in Eosinophilic Esophagitis", Journal of Immunology, 184(7):4033-4041.
Blanchard et al. (Sep. 19, 2006) "Eosinophilic Esophagitis: Pathogenesis, Genetics, and Therapy", The Journal of Allergy and Clinical Immunology, 118(5):1054-1059.
Blanchard et al. (Feb. 2006) "Eotaxin-3 and a Uniquely Conserved Gene-Expression Profile in Eosinophilic Esophagitis", Journal of Clinical investigation, 116(2):536-547.
Blanchard et al. (Dec. 2005) "Eotaxin-3/CCL26 Gene Expression in Intestinal Epithelial Cells is Up-regulated by Interleukin-4 and Interleukin-13 via the Signal Transducer and Activator of Transcription 6", The International Journal of Biochemistry & Cell Biology, 37(12):2559-2573.
Blanchard et al. (Dec. 2007) "IL-13 Involvement in Eosinophilic Esophagitis: Transcriptome Analysis and Reversibility with Glucocorticoids", Journal of Allergy and Clinical Immunology, 120(6):1292-1300.
Blanchard et al. (Jan. 2007) "II-13 is Overexpressed in Eosinophilic Esophagitis and Induces Eotaxin-3 Expression in Esophageal Epithelial Cells", The Journal of Allergy and Clinical Immunology, S240, 1 page.
Blanchard et al. (Aug. 24, 2005) "Inhibition of Human Interleukin-13-induced Respiratory and Oesophageal Inflammation by Anti-human-interleukin-13 Antibody (CAT-354)", Clinical and Experimental Allergy, 35(8):1096-1103.
Blanchard et al. (Jul. 2008) "Periostin Facilitates Eosinophil Tissue Infiltration in Allergic Lung and Esophageal Responses", Mucosal Immunology, 1(4):289-296.
Blennow Kaj (Apr. 2004) "Cerebrospinal Fluid Protein Biomarkers for Alzheimer's Disease", NeuroRx, 1(2):213-225.
Bochner et al. (Jul. 2010) "What Targeting the Eosinophil has Taught us About their Role in Diseases", The Journal of Allergy and Clinical Immunology, 126(1):16-25.
Boeuf et al. (Mar. 4, 2005) "CyProQuant-PCR: A Real Time RT-PCR Technique for Profiling Human Cytokines, Based on External RNA Standards, Readily Automatable for Clinical Use", BMC Immunology, 6:14 pages.
Bonini et al. (Oct. 1, 1996) "Circulating Nerve Growth Factor Levels are Increased in Humans with Allergic Diseases and Asthma", Proceedings of the National Academy of Sciences of the United States of America, 93 (20):10955-10960.
Boon et al. (Oct. 23, 2003) "Comparison of Medulloblastoma and Normal Neural Transcriptomes Identifies a Restricted Set of Activated Genes", Oncogene, 22(48):7687-7694.
Branford et al. (Jul. 27, 2012) "Opioid genetics: the key to personalized pain control?", Clinical Genetics, 82(4):301-310.
Brightling et al. (Jan. 2010) "Interleukin-13: Prospects for New Treatments", Clinical & Experimental Allergy, 40(1):42-49.
Brodeur et al. (Jan. 1997) "Expression of TrkA, TrkB and TrkC in Human Neuroblastomas", Journal of Neuro-Oncology, 31(1-2):49-55.
Broide et al. (Mar. 2011) "Advances in Mechanisms of Asthma, Allergy, and Immunology in 2010", The Journal of Allergy and Clinical Immunology, 127(3):689-695.
Broide et al. (2009) "Immunomodulation of Allergic Disease", Annual Review of Medicine, 60:279-291.
Buitenhuis et al. (Jun. 1, 2005) "Differential Regulation of Granulopoiesis by the Basic Helix-loop-helix Transcriptional Inhibitors Id1 and Id2", Blood, 105(11):4272-4281.
Bullens et al. (Nov. 3, 2006) "IL-17 mRNA in Sputum of Asthmatic Patients: Linking T Cell Driven Inflammation and Granulocytic Influx?", Respiratory Research, 7(1):9 pages.
Bullock et al. (Jul. 2007) "Interplay of Adaptive Th2 Immunity with Eotaxin-3/c-C Chemokine Receptor 3 in Eosinophilic Esophagitis", Journal of Pediatric Gastroenterology and Nutrition, 45(1):22-31.
Burnett et al. (Jan. 27, 2012) "RNA-based Therapeutics: Current Progress and Future Prospects", Chemistry & Biology, 19(1):60-71.
Buscaglia et al. (Jun. 2011) "Apoptosis and the Target Genes of MicroRNA-21", Chinese Journal of Cancer, 30(6):371-380.
Busse et al. (Apr. 2010) "A Review of Treatment with Mepolizumab, an Anti-il-5 Mab, in Hypereosinophilic Syndromes and Asthma", The Journal of Allergy and Clinical Immunology, 25(4):803-813.
Cai et al. (Mar. 2017) "The Imprinted H19 Noncoding RNA is a Primary MicroRNA Precursor", RNA, 13(3):313-316.
Caldwell et al. (Sep. 2017) "Cadherin 26 is an alpha integrin-binding epithelial receptor regulated during allergic inflammation", Mucosal Immunology, 10(5):1190-1201.
Caldwell et al. (Feb. 2011) "Global Gene Expression Profile Analysis in Eosinophilic Gastritis Identifies CDH26", The Journal of Allergy and Clinical Immunology, Abstract 831, 127(2):1 page.
Caldwell et al. (Apr. 2010) "Glucocorticoid-regulated Genes in Eosinophilic Esophagitis: A Role for FKBP51", American Academy of Allergy, Asthma & Immunology, 125(4):879-888.
Cameron et al. (Mar. 2000) "Evidence for Local Eosinophil Differentiation Within Allergic Nasal Mucosa: Inhibition with Soluble IL-5 Receptor", The Journal of Immunology, 164(3):1538-1545.
International Search Report and Written Opinion of the International Searching Authority mailed on Jul. 8, 2019 for International Application No. PCT/US2019/028076, filed Apr. 18, 2019, 15 pages.
Rochman et al., Direct Action of Thymic Stromal Lymphopoietin on Activated Human CD4+ T Cells, J Immunol., Jun. 1, 2007 (Jun. 1, 2007), vol. 178, No. 11, pp. 6720-6724.
Extended European Search Report for EP Application No. 15828951.2, mailed on Nov. 16, 2017, 8 pages.
Extended European Search Report issued in European Application No. 16885429.7, mailed on Jul. 23, 2019, 15 pages.
Wen et al. (Aug. 23, 2013) "Molecular diagnosis of eosinophilic esophagitis by gene expression profiling", Gastroenterology, 145(6):19 Pages.
International Preliminary Report on Patentability received for PCT International Application No. PCT/US16/68238, mailed on Jul. 26, 2018, 7 pages.
Rothenberg et al. (Apr. 21, 2016) "Humanized anti-IL-5 Antibody Therapy" Cell, 165(3):1 page.
International Search Report for PCT Application No. PCT/US2006/016948, filed May 3, 2006, 1 page.
International Search Report mailed on Sep. 9, 2016 for International Application No. PCT/US2016/034185, filed May 25, 2016, 8 pages.
International Search Report received for PCT Patent International Application No. PCT/US16/68238, mailed on Mar. 27, 2017, 8 pages.
International Search Report received for PCT Patent International Application No. PCT/US2014/039357, mailed on Sep. 24, 2014, 8 pages.
International Search Report received for PCT Patent International Application No. PCT/US2014/049301, mailed on Dec. 8, 2014, 8 pages.
International Search Report received for PCT Patent International Application No. PCT/US2015/017134, mailed on May 6, 2015, 11 pages.
International Search Report received in connection with PCT/US2005/044456, mailed on Dec. 7, 2006, 7 pages.
Dellon et al. (May 1, 2014) "59 Immunohistochemical Evidence of Inflammation is Similar in Patients With Eosinophilic Esophagitis and PPI-Responsive Esophageal Eosinophilia: A Prospecitve Cohort Study", Gastroenterology, 146(5):S17.
Zuo et al. (Jul. 1, 2010) "IL-13 Induces Esophageal Remodeling and Gene Expression by an Eosinophil-Independent, IL-13Rα2—Inhibited Pathway", The Journal of Immunology, 185(1):660-669.
Zimmermann et al. (Apr. 30, 1999) "CC Chemokine Receptor-3 Undergoes Prolonged Ligand-induced Internalization", Journal of Biological Chemistry, 274(18):12611-12618.

(56) References Cited

OTHER PUBLICATIONS

Abidi et al. (2008) "Eosinopenia is a Reliable Marker of Sepsis on Admission to Medical Intensive Care Units", Critical Care, R59, 12(2):10 pages.
Abonia et al. (2012) "Eosinophilic Esophagitis: Rapidly Advancing Insights", Annual Review of Medicine, 63:421-434.
Abonia et al. (Jul. 2010) "Involvement of Mast Cells in Eosinophilic Esophagitis", The Journal of Allergy and Clinical Immunology, 126(1):140-149.
Aceves et al. (Jan. 2007) "Esophageal Remodeling in Pediatric Eosinophilic Esophagitis", The Journal of Allergy and Clinical Immunology, 119(1):206-212.
Aceves et al. (Dec. 2010) "Mast Cells Infiltrate the Esophageal Smooth Muscle in Patients with Eosinophilic Esophagitis, Express TGF-β1, and Increase Esophageal Smooth Muscle Contraction", The Journal of Allergy and Clinical Immunology, e4, 126(6):1198-204.
Ackerman et al. (Apr. 26, 2002) "Charcot-Leyden Crystal Protein (Galectin-10) is Not a Dual Function Galectin with Lysophospholipase Activity but Binds a Lysophospholipase Inhibitor in a Novel Structural Fashion", Journal of Biological Chemistry, 277(17):14859-14868.
Adachi et al. (Dec. 15, 2007) "Transduction of Phosphatase and Tensin Homolog Deleted on Chromosome 10 into Eosinophils Attenuates Survival, Chemotaxis, and Airway Inflammation", The Journal of Immunology, 179(12):8105-8111.
Akuthota et al. (2011) "Eosinophils: Offenders or General Bystanders in Allergic Airway Disease and Pulmonary Immunity?", Journal of Innate Immunity, 3(2):113-119.
Alexander Jeffreya (May 2014) "Topical Steroid Therapy for Eosinophilic Esophagitis", Gastroenterology & Hepatology, 10(5):327-329.
Allakhverdi et al. (Feb. 2009) "CD34+ Hemopoietic Progenitor Cells are Potent Effectors of Allergic Inflammation", Journal of Allergy and Clinical Immunology, 123(2):472-478.
Anderson et al. (Sep. 2011) "Evaluation of a morphine maturation model for the prediction of morphine clearance in children", British Journal of Clinical Pharmacology, 72(3):518-520.
Angus et al. (Jul. 2009) "Epidemiology of Severe Sepsis in the United States: Analysis of Incidence, Outcome, and Associated Costs of Care", Critical Care Medicine, 29(7):1303-1310.
Anonymous (Jul. 7, 2015) "TaqMan(R) Human Micro RNA Arrays", 2 pages.
Anthony et al. (Dec. 2007) "Protective Immune Mechanisms in Helminth Infection", Nature Reviews Immunology, 7(12):975-987.
April et al. (Dec. 3, 2009) "Whole-Genome Gene Expression Profiling of Formalin-Fixed, Paraffin-Embedded Tissue Samples", Plos One, e8162, 4(12):10 pages.
Arefi et al. (Sep. 2012) "Response to Imatinib Mesylate in Patients with Hypereosinophilic Syndrome", International Journal of Hematology, 96(3):320-326.
Armour et al. (Mar. 31, 2010) "Expression of Human FcγRIIIa as a GPI-linked Molecule on CHO Cells to Enable Measurement of Human IgG Binding", Journal of Immunological Methods, 354(1-2):20-33.
Arroyo et al. (Mar. 22, 2011) "Argonaute2 Complexes Carry a Population of Circulating MicroRNAs Independent of Vesicles in Human Plasma", Proceedings of the National Academy of Sciences of the United States of America, 108(12):5003-5008.
Ishihara, Shunji et al. "Serum Biomarkers for the Diagnosis of Eosinophilic Esophagitis and Eosinophilic Gastroenteritis." Internal medicine (Tokyo, Japan) vol. 56,21 (2017): 2819-2825.
Shoda, Tetsuo et al. "Sera of patients with infantile eosinophilic gastroenteritis showed a specific increase in both thymic stromal lymphopoietin and IL-33 levels." The Journal of allergy and clinical immunology vol. 138, 1 (2016): 299-303.
Kaur et al. (Jul. 1, 2002) "Rofecoxib Inhibits Cyclooxygenase 2 Expression and Activity and Reduces Cell Proliferation in Barrett's Esophagus", Gastroenterology, 123(1):60-67.
Kelly et al. (Apr. 9, 2012) "More codeine fatalities after tonsillectomy in North American children", Pediatrics, 129(5):e1343-1347.
Kerstjens et al. (Oct. 2019) "Airway Pharmacology: Treatment Options and Algorithms to Treat Patients with Chronic Obstructive Pulmonary Disease", Journal of Thoracic Disease, 11(S17):S2200-S2209.
Kihara et al. (Sep. 1, 2001) "Prediction of Sensitivity of Esophageal Tumors to Adjuvant Chemotherapy by CDNA Microarray Analysis of Gene-expression Profiles", Cancer Research, 61(17):6474-6479.
Kim et al. (2004) "Microarray Applications in Cancer Research", Cancer Research and Treatment, 36(4):207-213.
Kim et al. (Dec. 2004) "Rebound Eosinophilia after Treatment of Hypereosinophilic Syndrome and Eosinophilic Gastroenteritis with Monoclonal Anti-IL-5 Antibody SCH55700", The Journal of Allergy and Clinical Immunology, 114(6):1449-1455.
Kledal et al. (Sep. 12, 1997) "A Broad-Spectrum Chemokine Antagonist Encoded by Kaposi's Sarcoma-Associated Herpesvirus", Science, 277(5332):1656-1659.
Klingelhöfer et al. (Nov. 2002) "Dynamic Interplay Between Adhesive and Lateral E-Cadherin Dimers", Molecular and Cellular Biology, 22(21):7449-7458.
Komiya et al. (Oct. 2003) "Concerted Expression of Eotaxin-1, Eotaxin-2, and Eotaxin-3 in Human Bronchial Epithelial Cells", Cellular Immunology, 225(2):91-100.
Kong et al., (Jan. 2012) "MicroRNA-375 Inhibits Tumour Growth and Metastasis in Oesophageal Squamous Cell Carcinoma Through Repressing Insulin-like Growth Factor 1 Receptor", Gut., 61(1):33-42.
Konikoff et al. (Nov. 2006) "A Randomized, Double-blind, Placebo-controlled Trial of Fluticasone Propionate for Pediatric Eosinophilic Esophagitis", Gastroenterology, 131(5):1381-1391.
Konturek et al. (Aug. 2004) "Activation of NFκB Represents the Central Event in the Neoplastic Progression Associated with Barrett's Esophagus: A Possible Link to the Inflammation and Overexpression of COX-2, PPARγ and Growth Factors", Digestive Diseases and Sciences, 49(7-8):1075-1083.
Kottyan et al. (Jul. 13, 2014) "Genome-wide Association Analysis of Eosinophilic Esophagitis Provides Insight into the Tissue Specificity of this Allergic Disease", Nature Genetics, 46(8):895-900.
Kouro et al. (Dec. 2009) "IL-5- and Eosinophil-mediated Inflammation: From Discovery to Therapy", International Immunology, 21(12):1303-1309.
Krichevsky et al. (Jan. 2009) "MIR-21: A Small Multi-faceted RNA", Journal of Cellular and Molecular Medicine, 13(1):39-53.
Krutzfeldt et al. (Dec. 1, 2005) "Silencing of MicroRNAs in Vivo with 'Antagomirs'", Nature, 438 (7068):685-689.
Kumar et al. (Nov. 2011) "Let-7 microRNA-mediated Regulation of IL-13 and Allergic Airway Inflammation", The Journal of Allergy and Clinical Immunology, e10, 128(5):1077-1085.
Kuperman et al. (Aug. 2002) "Direct Effects of Interleukin-13 on Epithelial Cells Cause Airway Hyperreactivity and Mucus Overproduction in Asthma", Nature Medicine, 8(8):885-889.
Kuperman et al. (Mar. 16, 1998) "Signal Transducer and Activator of Transcription Factor 6 (Stat6)-deficient Mice are Protected from Antigen-induced Airway Hyperresponsiveness and Mucus Production", Journal of Experimental Medicine, 187(6):939-948.
Laprise et al. (Mar. 23, 2004) "Functional Classes of Bronchial Mucosa Genes that are Differentially Expressed in Asthma", BMC Genomics, 5(1):10 pages.
Lavigne et al. (Nov. 12, 2004) "Human Bronchial Epithelial Cells Express and Secrete MMP-12", Biochemical and Biophysical Research Communications, 324(2):534-546.
Lee et al. (Apr. 2010) "Eosinophils in Health And Disease: The LIAR Hypothesis", Clinical & Experimental Allergy, 40 (4):563-575.
Lee et al. (Jan. 2006) "ERK1/2 Mitogen-activated Protein Kinase Selectively Mediates IL-13-induced Lung Inflammation and Remodeling in Vivo", Journal of Clinical Investigation, 116(1):163-173.
Lee et al. (Oct. 2001) "Interleukin-13 Induces Dramatically Different Transcriptional Programs in Three Human Airway Cell Types", American Journal of Respiratory Cell and Molecular, 25(4):474-485.

(56) References Cited

OTHER PUBLICATIONS

Lei et al. (Mar. 2007) "Transcriptional Regulation of Trk Family Neurotrophin Receptors", Cellular and Molecular Life Sciences, 64(5):522-532.
Leigh et al. (Apr. 1, 2004) "Type 2 Cytokines in the Pathogenesis of Sustained Airway Dysfunction and Airway Remodeling in Mice", American Journal of Respiratory and Critical Care Medicine, 169(7):860-867.
Leschziner et al. (Sep. 12, 2006) "ABCB1 genotype and PGP expression, function and therapeutic drug response: a critical review and recommendations for future research", The Pharmacogenomics Journal, 7(3):154-179.
Letunic et al. (Jan. 2012) "Smart 7: Recent Updates to the Protein Domain Annotation Resource", Nucleic Acids Research, 40:D302-D305.
Levi-Montalcini R. (Sep. 4, 1987) "The Nerve Growth Factor 35 Years Late", Science, 237 (4819):1154-1162.
Li et al. (Oct. 2011) "Epigenetic Silencing of microRNA-375 Regulates PDKI Expression in Esophageal Cancer", Digestive Diseases and Sciences, 56(10):2849-2856.
Li et al. (Mar. 31, 2011) "miR-223 Regulates Migration and Invasion by Targeting Artemin in Human Esophageal Carcinoma", Journal of Biomedical Science, 18(1):9 pages.
Liacouras et al. (Jul. 2011) "Eosinophilic Esophagitis: Updated Consensus Recommendations for Children and Adults", Journal of Allergy and Clinical Immunology, 128(1):3-26.
Liacouras et al. (Sep. 2007) "Summary of the First International Gastrointestinal Eosinophil Research Symposium", Journal of Pediatric Gastroenterology and Nutrition, 45(3):370-391.
Liesveld Jane (Dec. 2018) "Hypereosinophilic Syndrome", MSD Manual Professional Version, 5 Pages.
Lim et al. (Jan. 1, 2014) "Demethylation of the Human Eotaxin-3 Gene Promoter Leads to the Elevated Expression of Eotaxin-3", Journal of Immunology, 192(1):466-474.
Lim et al. (Apr. 15, 2011) "Epigenetic Regulation of the IL-13-induced Human Eotaxin-3 Gene by CREB-binding Protein-mediated Histone 3 Acetylation", Journal of Biological Chemistry, 286(15):13193-13204.
Lin et al. (Mar. 31, 2011) "miR-142-3p as a Potential Prognostic Biomarker for Esophageal Squamous Cell Carcinoma", Journal of Surgical Oncology, 105(2):175-182.
Linch et al. (Nov. 2009) "Mouse Eosinophils Possess Potent Antibacterial Properties in Vivo", Infection and Immunity, 77(11):4976-4982.
Linch et al. (Jun. 2011) "The Role of Eosinophils in Non-parasitic Infections", Endocrine, Metabolic & Immune Disorders—Drug Targets, 11(2):165-172.
Lipkin Stefanien. (Apr. 1979) "Eosinophil Counts in Bacteremia", Archives of Internal Medicin, 139(4):490-491.
Liu et al. (Feb. 2012) "Role of microRNA let-7 and Effect to HMGA2 in Esophageal Squamous Cell Carcinoma", Molecular Biology Reports, 39(2):1239-1246.
Livak et al. (2001) "Analysis of Relative Gene Expression Data using Real-Time Quantitative PCR and the 2-Delta DeltaCT Method", Methods, 25:402-408.
Lo et al. (Dec. 16, 2011) "Identification of a Novel Mouse p53 Target Gene DDA3", Oncogene, 18(54):7765-7774.
Long et al. (Jun. 1, 2002) "Disruption of the NAD(P)H:quinone Oxidoreductase 1 (NQO1) Gene in Mice Causes Myelogenous Hyperplasia", Cancer Research, 62(11):3030-3036.
Lovinsky-Desir et al. (Jun. 2012) "Epigenetics, Asthma, and Allergic Diseases: A Review of the Latest Advancements", Current Allergy and Asthma Reports, 12(3):211-220.
Lu et al. (2013) "Diagnostic, functional, and therapeutic roles of microRNA in allergic diseases", Journal of Allergy and Clinical Immunology, 132(1):3-13.
Lu et al. (Sep. 17, 2010) "Function of miR-146a in Controlling Treg Cell-mediated Regulation of Th1 Responses", Cell, 142(6):914-929.

Lu et al. (Jul. 16, 2012) "MicroRNA Profiling in Mucosal Biopsies of Eosinophilic Esophagitis Patients Pre and Post Treatment with Steroids and Relationship with mRNA Targets", PLoS One, e40676, 7(7):11 pages.
Lu et al. (Apr. 2012) "MicroRNA signature in Patients with Eosinophilic Esophagitis, Reversibility with Glucocorticoids, and Assessment as Disease Biomarkers", The Journal of Allergy and Clinical Immunology, e9, 129(4):1064-1075.
Lu et al. (Apr. 15, 2009) "MicroRNA-21 is Up-Regulated in Allergic Airway Inflammation and Regulates IL-12p35 Expression", Journal of Immunology, 182(8):4994-5002.
Caramori et al. (Aug. 2005) "Anti-inflammatory Mechanisms of Glucocorticoids Targeting Granulocytes", Current Drug Targets—Inflammation & Allergy, 4(4):455-463.
Carriere et al. (Jan. 2, 2007) "IL-33, the IL-1-like Cytokine Ligand for ST2 Receptor, is a Chromatin-associated Nuclear Factor in Vivo", Proceedings of the National Academy of Sciences of the United States of America, 104(1):282-287.
Carthew et al. (Feb. 20, 2009) "Origins and Mechanisms of miRNAs and siRNAs", Cell, 136(4):642-655.
Chehade et al. (Jun. 2010) "Food Allergy and Eosinophilic Esophagitis", Current Opinion in Allergy and Clinical Immunology, 10(3):231-237.
Chen et al. (Jul. 1, 2009) "ToppGene Suite for Gene List Enrichment Analysis and Candidate Gene Prioritization", Nucleic Acids Research, 37(Suppl. 2):W305-W311.
Cheverud Jamesm. (Jul. 2001) "A Simple Correction for Multiple Comparisons in Interval Mapping Genome Scans", Heredity, 87(Pt 1):52-58.
Cho et al. (Mar. 24, 2006) "Role of Early Growth Response-1 (Egr-1) in Interleukin-13-induced Inflammation and Remodeling", Journal of Biological Chemistry, 281(12):8161-8168.
Chu et al. (Jan. 9, 2011) "Eosinophils are Required for the Maintenance of Plasma Cells in the Bone Marrow", Nature Immunology, 12(2):151-159.
Clavijo et al. (Mar. 12, 2011) "A sensitive assay for the quantification of morphine and its active metabolites in human plasma and dried blood spots using high-performance liquid chromatography-tandem mass spectrometry", Analytical and Bioanalytical Chemistry, 400(3):715-728.
Cohen et al. (Aug. 2012) "Pharmacogenetics in perioperative medicine", Current opinion in anaesthesiology, 25(4):419-427.
Collins et al. (Jun. 2008) "Clinical, Pathologic, and Molecular Characterization of Familial Eosinophilic Esophagitis Compared With Sporadic Cases", Clinical Gastroenterology and Hepatology, 6(6):621-629.
Collins et al. (Oct. 2005) "Online Selection of Discriminative Tracking Features", IEEE Transactions on Pattern Analysis and Machine Intelligence, 27(10):1631-1643.
Collison et al. (Jul. 2011) "Inhibition of House Dust Mite-induced Allergic Airways Disease by Antagonism of MicroRNA-145 is Comparable to Glucocorticoid Treatment", The Journal of Allergy and Clinical Immunology, e4, 128(1):160-167.
Corren et al. (Sep. 22, 2011) "Lebrikizumab Treatment in Adults with Asthma", The New England Journal of Medicine, 365(12):1088-1098.
Crews et al. (Jan. 29, 2014) "Clinical Pharmacogenetics Implementation Consortium Guidelines for Cytochrome P450 2d6 Genotype and Codeine Therapy", Clinical Pharmacology & Therapeutics, 95(4):376-382.
Czajkowsky et al. (Oct. 2012) "Fc-fusion Proteins: New Developments and Future Prospectives", EMBO Molecular Medicine, 4(10):1015-1028.
D'Agostini et al. (Jul. 2005) "Antitumour Effect of Om-174 and Cyclophosphamide on Murine B16 Melanoma in Different Experimental Conditions", International Immunopharmacology, 5(7-8):1205-1212.
Dalal et al. (Oct. 31, 1997) "Molecular Characterization of Neurotrophin Expression and the Corresponding Tropomyosin Receptor Kinases (trks) in Epithelial and Stromal Cells of the Human Prostate", Molecular and Cellular Endocrinology, 134(1):15-22.

(56) References Cited

OTHER PUBLICATIONS

Davis Carla M. (Feb. 11, 2011) "Diagnosis and Treatment of Eosinophilic Gastrointestinal Disorders", Pediatric Allergy, Immunology, and Pulmonology, 23(4):237-242.
De Bruin et al. (Oct. 7, 2010) "Eosinophil Differentiation in the Bone Marrow is Inhibited by T Cell-derived IFN-y", Blood, 116(14):2559-2569.
Debrosse et al. (Jul. 2010) "Identification, Epidemiology and Chronicity of Pediatric Esophageal Eosinophilia from 1982-1999", The Journal of Allergy and Clinical Immunology, 126(1):112-119.
Lexmond et al. (Aug. 2013) "Elevated Levels Of leukotriene C4 Synthase mRNA Distinguish a Subpopulation of Eosinophilic Oesophagitis Patients", Clinical & Experimental Allergy, 43(8):902-913.
Dellon et al. (Oct. 22, 2013) "Clinical and endoscopic characteristics do not reliably differentiate PPI-responsive esophageal eosinophilia and eosinophilic esophagitis in patients undergoing upper endoscopy: a prospective cohort study", The American Journal of Gastroenterology, 108(12):1854-1860.
Dellon et al. (Jul. 2012) "Eosinophilic Esophagitis: Diagnostic Tests and Criteria", Current Opinion in Gastroenterology, 28(4):382-388.
Dellon et al. (Feb. 2011) "Tryptase Staining of Mast Cells may Differentiate Eosinophilic Esophagitis from Gastroesophageal Reflux Disease", The American Journal of Gastroenterology, 106(2):264-271.
Dent et al. (Nov. 1, 1990) "Eosinophilia in Transgenic Mice Expressing Interleukin 5", Journal of Experimental Medicine, 172(5):1425-1431.
Descamps et al. (Jul. 2005) "Expression of Nerve Growth Factor Receptors and their Prognostic Value in Human Breast Cancer", Oncology Reports, 14(1):161-171.
Dewson et al. (Oct. 1, 2001) "Interleukin-5 Inhibits Translocation of Bax to the Mitochondria, Cytochrome C Release, and Activation of Caspases in Human Eosinophil", Blood, 98(7):2239-2247.
Dohrman et al. (Aug. 1997) "Ethanol Reduces Expression of the Nerve Growth Factor Receptor, But not Nerve Growth Factor Protein Levels in the Neonatal Rat Cerebellum", Alcoholism: Clinical and Experimental Research, 21(5):882-893.
Donato et al. (Jan. 1, 2002) "Human HTm4 is a Hematopoietic Cell Cycle Regulator", Journal of Clinical Investigation, 109(1):51-58.
Driss et al. (Apr. 2, 2009) "TLR2-dependent Eosinophil Interactions with Mycobacteria: Role of Alpha-defensins", Blood, 113(14):3235-3244.
Dyer et al. (Sep. 15, 2008) "Functionally Competent Eosinophils Differentiated Ex Vivo in High Purity From Normal Mouse Bone Marrow", Journal of Immunology, 181(6):4004-4009.
Dyer et al. (Jan. 1, 2009) "Generation of Eosinophils from Unselected Bone Marrow Progenitors: Wild-type, TLR- and Eosinophil-deficient Mice", The Open Immunology Journal, 2:163-167.
Dyer et al. (Jun. 1, 2010) "Mouse and Human Eosinophils De Granulate in Response to Platelet-activating Factor (PAF) and C21 LysoPAF via a PAF receptor-independent Mechanism: Evidence for a Novel Receptor", Journal of Immunology, 184(11):6327-6334.
Dyer et al. (Sep. 24, 2009) "Pneumoviruses Infect Eosinophils and Elicit MyD88-dependent Release of Chemoattractant Cytokines and Interleukin-6", Blood, 114(13):2649-2656.
Ehlers et al. (1991) "Differentiation of T Cell Lymphokine Gene Expression: The in Vitro Acquisition of T Cell Memory", Journal of Experimental Medicine, 173(1):25-36.
Eissing et al. (Feb. 1, 2012) "Pharmacogenomics of Codeine, Morphine, and Morphine-6-Glucuronide: Model-Based Analysis of the Influence of CYP2D6 Activity, UGT2B7 Activity, Renal Impairment, and CYP3A4 Inhibition", Molecular Diagnosis & Therapy, 16(1):43-53.
Elsner (Nov. 1992) "The CC Chemokine Antagonist Met-Rantes Inhibits Eosinophil Effector Functions through the Chemokine Receptors CCR1 and CCR3", European Journal of Immunology, 27(11):2892-2998.
Fahy et al. (Nov. 15, 2001) "Remodeling of the Airway Epithelium in Asthma", American Journal of Respiratory and Critical Care Medicine, 164(10 Pt 2):S46-S51.
Fardet et al. (Jan. 22, 2006) "Severe Strongyloidiasis in Corticosteroid-treated Patients: Case Series and literature Review", Journal of Infection, 54(1):18-27.
Faubion et al. (Jul. 1998) "Treatment of Eosinophilic Esophagitis with Inhaled Corticosteroids", Journal of Pediatric Gastroenterology and Nutrition, 27(1):90-93.
Festuccia et al. (Jan. 2007) "Tyrosine Kinase Inhibitor CEP-701 Blocks the NTRK1/NGF Receptor and Limits the Invasive Capability of Prostate Cancer Cells in Vitro", International Journal of Oncology, 30(1):193-200.
Flower et al. (Nov. 16, 1999) "Modelling G-protein-coupled Receptors for Drug Design", Biochimica et Biophysica Acta, 1422(3):207-234.
Fox et al. (Aug. 2002) "Eosinophilic Esophagitis: It's Not Just Kid's Stuff", Gastrointestinal Endoscopy, 56(2):260-270.
Freund-Michel et al. (Jan. 2008) "The Nerve Growth Factor and its Receptors in Airway Inflammatory Diseases", Pharmacology & Therapeutics, 117(1):52-76.
Frossard et al. (Oct. 1, 2004) "Nerve Growth Factor and its Receptors in Asthma and Inflammation", European Journal of Pharmacology, 500(1-3):453-465.
Fuentebella et al. (Sep. 2010) "Increased Number of Regulatory T Cells in Esophageal Tissue of Patients with Eosinophilic Esophagitis in Comparison to Gastro Esophageal Reflux Disease and Control Groups", Journal of Pediatric Gastroenterology and Nutrition, 51(3):283-589.
Fukada et al. (Jul. 2013) "OCT1 genetic variants influence the pharmacokinetics of morphine in children", Pharmacogenomics, 14(10):1141-1151.
Fukao (Jun. 2007) "An Evolutionarily Conserved Mechanism for MicroRNA-223 Expression Revealed by MicroRNA Gene Profiling", Cell, 129(3):617-631.
Fukuda et al. (Feb. 2013) "Oral Session II-A (OII-A) Special Populations 3:45 pm-4:45 pm", Clinical Pharmacology & Therapeutics, 93:S49-S51.
Dellon, Evan S et al. "Esophageal dilation in eosinophilic esophagitis: safety and predictors of clinical response and complications." Gastrointestinal endoscopy vol. 71,4 (2010): 706-12. doi:10.1016/j gie.2009.10.047.
Molina-Infante et al., 2016—"Proton pump inhibitor-responsive oesophageal eosinophilia: an entity challenging current diagnostic criteria for eosinophilic oesophagitis" Gut—65:524-531.
Chen et al., "Serine Protease Inhibitors Nafamostat Mesilate and Gabexate Mesilate Attenuate Allergen-Induced Airway Inflammation and Eosinophilia in a murine Model of Asthma," The Journal of Allergy and Clinical Immunology, vol. 118, No. 1: 105-112 (Jul. 2006).
Frigas et al., "The eosinophil and the pathophysiology of asthma," The Journal of Allergy and Clinical Immunology, vol. 77, No. 4: 527-537 (Apr. 1986).
Zhou et al., "Stuctural study of the uPA-nafamostat complex reveals a covalent inhibitory mechanism of nafamostat," Biophysical Journal, vol. 121, No. 20: 3940-3949 (Aug. 2022).
European Office Action in EP Application No. 22162120.4, dated Mar. 27, 2025, 11 pages.

* cited by examiner

BLOOD BIOMARKER FOR EOSINOPHILIC GASTROINTESTINAL DISORDERS

CROSS-REFERENCE TO RELATED APPLICATIONS

This application is a national stage entry, filed under 35 U.S.C. § 371, of International Application No. PCT/US2019/028076, filed on Apr. 18, 2019, which claims the benefit of U.S. Provisional Application No. 62/660,308, filed Apr. 20, 2018, the entire disclosure of which is incorporated herein by reference in its entirety.

STATEMENT REGARDING FEDERALLY-SPONSORED RESEARCH

This invention was made with U.S. Government support under R01 AI 124355 awarded by the National Institutes of Health. The U.S. Government has certain rights in the invention.

FIELD OF THE INVENTION

The disclosure relates to methods for diagnosing, treating, and monitoring eosinophilic gastrointestinal disorders using a blood-based biomarker assay.

BACKGROUND OF THE INVENTION

The cytokine thymic stromal lymphopoietin (TSLP) is one of the major pro-inflammatory and pro-allergic cytokines in humans. It is expressed primarily by epithelial cells, especially in the lung and skin and has been linked with the initiation and progression of allergic inflammatory disease. For review of TSLP and allergic disease, see Ziegler, *J. Allergy Clin Immunol.* 2012 130:845.

Presently, a definitive diagnosis of eosinophilic gastrointestinal disorders (EGID) such as eosinophilic esophagitis (EoE) and eosinophilic gastritis (EG) depends upon a costly and uncomfortable endoscopic procedure followed by histologic examination of the tissue biopsy to assess the number of eosinophils per high power field, which remains the 'gold standard' of diagnosis. There is a need for improved assays to detect, diagnosis and monitor EGID to improve clinical care in human patients. The present disclosure addresses this need.

SUMMARY OF THE INVENTION

The present invention is based, in part, on the surprising discovery of a distinct subpopulation of memory CD4+T helper cells present in the peripheral blood of human patients with active eosinophilic gastrointestinal disorder (EGID) that is responsive to thymic stromal lymphopoietin (TSLP). Moreover, TSLP responsiveness, as determined according to the methods described here, correlates with disease severity, providing the basis for a blood-based assay for the care and management of EGID. Accordingly, the disclosure provides blood-based biomarker assays, and related compositions and methods, for the diagnosis, treatment, and monitoring of EGID in human subjects.

The disclosure provides methods for detecting TSLP-responsive cells in human blood, the methods comprising
  contacting cells in vitro with TSLP, wherein the cells are previously isolated from a sample of whole blood obtained from a human subject in need of treatment for an eosinophilic gastrointestinal disorder (EGID), and
  detecting one or more analytes in the cells or secreted by the cells, the one or more analytes selected from phosphorylated signal transducer and activator of transcription 5 (pSTAT5), interleukin-5 (IL-5), and interleukin-13 (IL-13),
  wherein the detection of the one or more of the analytes indicates TSLP responsive cells in the blood of the human subject.

In embodiments, the detection of the one or more analytes is determined to be positive or negative based upon a predetermined threshold. In embodiments, a positive detection of the one or more analytes indicates TSLP responsive cells in the blood of the human subject.

In embodiments, the method for detecting TSLP-responsive cells in human blood is for use in a method for diagnosing or monitoring EGID in a human subject in need thereof.

In embodiments, the method further comprises determining an amount of the one or more analytes and determining whether the amount is above or below a diagnostic threshold, wherein an amount above the diagnostic threshold indicates an EGID status of active disease in a method for diagnosing, or disease progression in a method of monitoring EGID.

In embodiments, the cells are selected from peripheral blood mononuclear cells (PBMC), CD4+ T cells, and memory CD4+ T cells. In embodiments, the method further comprises a step of isolating a fraction of cells from the whole blood enriched for PBMC, CD4+ T cells, or memory CD4+ T cells.

In embodiments, the analyte is pSTAT5. In embodiments, the pSTAT5 is detected by a method comprising flow cytometry.

In embodiments, the analyte is IL-5 or IL-13 gene or protein expression. In embodiments, the IL-5 or IL-13 gene expression is detected by a method comprising a polymerase chain reaction (PCR), flow cytometry, or a chromatographic technique. In embodiments, the IL-5 or IL-13 protein expression is detected by a method comprising one or more of flow cytometry, immunoassay, and a chromatographic technique.

In embodiments, the EGID is eosinophilic esophagitis (EoE), eosinophilic gastritis (EG), or eosinophilic gastroenteritis (EGE).

In embodiments, the subject in need is characterized as presenting with clinical features selected from one or more of dysphagia, food impactions, vomiting, abdominal pain, refractory reflux symptoms, failure to thrive in young children, a diagnosis of an atopic allergic disorder, and a family member having an EGID diagnosis. In embodiments, the atopic allergic disorder is selected from asthma, atopic dermatitis, allergic rhinitis and allergic conjunctivitis.

In embodiments, the method further comprises a step of administering an EGID therapy to the subject in need. In embodiments, the EGID therapy is selected from proton pump inhibitor therapy, dietary therapy, anti-cytokine therapy, anti-ALOX15 therapy, anti-TSLP therapy, anti-eosinophil therapy, glucocorticoid therapy, and esophageal dilation. In embodiments, the EGID therapy comprises anti-TSLP therapy. In embodiments, the anti-TSLP therapy is an immunotherapy. In embodiments, the anti-TSLP therapy comprises anti-TSLP monoclonal antibody therapy.

The disclosure also provides a rapid assay for detecting a thymic stromal lymphopoietin (TSLP) responsive population of cells in human blood, the method comprising contacting cells in vitro with TSLP, wherein the cells are previously isolated from a sample of whole blood obtained from a human subject in need of treatment for an eosinophilic gastrointestinal disorder (EGID), and detecting phosphorylated signal transducer and activator of transcription 5 (pSTAT5) in the cells, wherein the presence of pSTAT5 indicates a TSLP responsive population of cells in the blood of the human subject. In embodiments, the assay may be performed within about 1-6 hours, preferably within about 2-4 hours.

In embodiments, the rapid assay is performed by a method comprising flow cytometric analysis of pSTAT5. In embodiments, the cells are selected from PBMC, CD4+ T cells, or memory CD4+ T cells, preferably memory CD4+ T cells. In embodiments, the method further comprises isolating PBMC, CD4+ T cells, or memory CD4+ T cells from the sample of whole blood.

DETAILED DESCRIPTION OF THE INVENTION

Figure 1A:
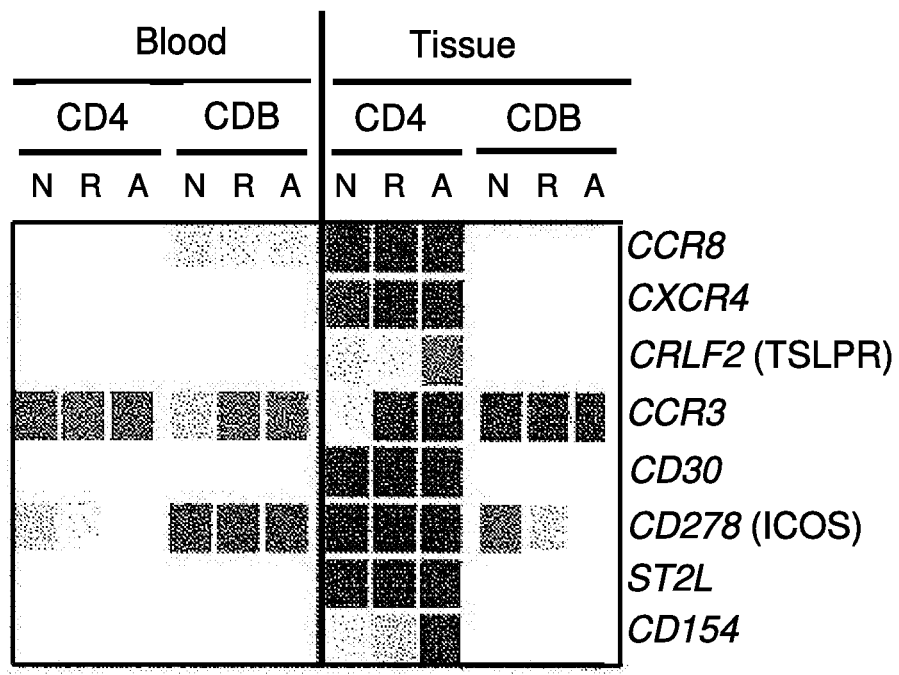
FIGS. 1A-B: A, flow cytometry analysis of $CD4^+$ and $CD8^±$-gated T cells from blood and biopsies of normal (N), EoE remission (R), and active EoE (A) patients to detect the expression of a panel of cytokine receptor genes. B, flow cytometric double plots of $CD3^+$ $CD4^+$-gated cells stained for TSLPR and CD45RO.

The inventors' discovery of TSLP-responsive memory CD4+T helper cells in the peripheral blood of human patients with active EGID, and the relationship to disease status, provides the basis for improved patient care in the form of a non-invasive blood-based assay for EGID status that can serve as an alternative or complement to endoscopy in the diagnosis and monitoring of EGID in human patients. The methods described here may advantageously form part of a therapeutic regimen effective to reduce the total number of endoscopies required to monitor disease and treat the EGID patient. In embodiments, the number of endoscopic procedures required may be reduced, e.g., from twice yearly to once per year or less.

Eosinophilic gastrointestinal disorders (EGID) are a diverse group of disorders characterized by increased eosinophil counts in one or more parts of the gastrointestinal tract in the absence of known causes for eosinophilia (e.g., secondary infections) or an underlying systemic inflammatory disease such as inflammatory bowel disease. EGID include disorders such as eosinophilic esophagitis (EoE), eosinophilic gastritis (EG), and eosinophilic gastroenteritis (EGE).

TSLP is one of the key pro-allergic cytokines associated with EGID, and in the context of EoE, a TSLP-elicited basophil response may contribute to pathogenesis. Noti et al., *Nature Med.* 2013 19:1005. Our laboratory previously reported elevated TSLP levels in the esophageal tissues of individuals with EoE. (Blanchard C., et al., *J. Clin. Invest.* 2006 116(2):536-547) and a strong association of single-nucleotide polymorphisms (SNPs) in the TSLP locus with susceptibility to EoE (Rothenberg M E., et al., *Nat. Genet.* 2010 42(4):289-291).

Although murine CD4+ T cells are known to respond to TSLP, freshly isolated human CD4+ T cells have little, if any, detectable TSLP receptor mRNA and are unresponsive to TSLP in vitro, although the cells do respond to IL-2 and IL-7 as evidenced by activation of signal transducer and activator of transcription 5 (STAT5), assayed by detection of phosphorylated STAT5 (pSTAT5) produced by the cells. Rochman I. et al., *J. Immunol.* 2007 178:6720-6724. The phosphorylation of STAT5 was previously identified as the immediate downstream signaling element induced by TSLP signaling through its receptor. Rochman et al., *Proc. Natl. Acad. Sci. USA* 2010 107:19455-19460. Isolated human CD4+ T cells can be "pre-activated" in vitro by stimulation with anti-CD3 and anti-CD28 antibodies which mediate TSLP receptor expression and induce cell responsiveness to in vitro stimulation with TSLP. Rochman et al., *J. Immunol.* 2007. However, prior to the current disclosure, it was not known that there were endogenous TSLP responsive cells present in the peripheral blood, or that these cells could be used as a biomarker of disease status in EGID.

Eosinophilic Gastrointestinal Disorders (EGID)

Although EGID are classified as "allergic disorders" they have distinct pathology compared to other allergic disorders such as asthma, atopic dermatitis, and celiac disease. The pathogenesis of EGID involves an immune/antigen driven Th2 response. CD4$^+$ T helper cells in the affected tissues produce increased amounts of pro-inflammatory Th2 cytokines including IL-4, IL-5, and IL-13, and these cells have been identified as the primary cellular sources of Th2 cytokines in the pathogenesis of EoE. Mitson-Salazar A., et al., *J. Allergy Clin. Immunol.* 2016; 137(3):907-918 e909; Wen et al., *J. Clin Invest.* 2019 Apr. 8; 130. pii: 125917. doi: 10.1172/JCI125917. In the context of the present disclosure, CD4+T helper cells may also be referred to interchangeably as "CD4+ T cells" or simply as "T helper cells", or "Th cells". Th2 cytokine transcripts and proteins have also been identified in EoE biopsy tissues and are implicated as key contributory factors in EGID, as evidenced by rodent EoE models and anti-IL-13 therapy in humans. Blanchard C., et al., *J. Allergy Clin. Immunol.* 2011 127(1):208-217; Hirano et al, *Gastroenterology* 2019 156(3):592-603.

Standard diagnosis of EGID is dependent upon quantitative assessment of eosinophils in the affected tissue, e.g., esophageal tissue for EoE or gastric tissue for EG. For example, a peak eosinophil count of ≥15 intraepithelial eosinophils in one high-power field [HPF] is the benchmark for EoE diagnosis. Tissue for diagnosis is obtained using an expensive and uncomfortable invasive endoscopy procedure. Typically, following diagnosis and the initiation of therapy, a patient will need to undergo endoscopy at least twice a year in order to monitor disease progression and determine therapeutic efficacy. The present methods provide an alternative to endoscopy in the diagnosis and management of EGID in the form of a simple blood-based assay.

Blood-Based Bioassays for EGID

The blood-based bioassays described here represent a significant improvement in patient care because they reduce the need for repeated endoscopy, which is both expensive and uncomfortable. In accordance with the methods described here, TSLP-responsive cells are detected in a sample of whole blood obtained from a human subject in need of diagnosis, treatment or monitoring for EGID. Responsiveness to TSLP is determined using an in vitro assay in which isolated cells are stimulated with TSLP for a suitable period of time to induce TSLP-receptor mediated signal transduction. The isolated cells may be peripheral blood mononuclear cells (PBMC), CD4+ T cells, or memory CD4+ T cells. After TSLP stimulation, the cells are assayed for the activation or expression of one or more TSLP-targeted proteins selected from phosphorylated STAT5 (pSTAT5), interleukin-5 (IL-5), and interleukin-13 (IL-13). The inventors have determined that the level of TSLP-responsive cells determined in accordance with the methods described here is positively correlated with EGID disease status in human patients, enabling the use of TSLP-responsiveness as a biomarker in the diagnosis and management of EGID.

In embodiments, the methods comprise the detection of cells positive for pSTAT5, for example using a method suitable for the detection of specific phosphoproteins, including flourescence activated cell sorting, or "FACS", also referred to as "flow cytometry", chromatography based techniques, and solid or liquid phase immunoassays. Exemplary techniques include Western blotting, affinity chromatography, thin layer chromatography, high pressure liquid chromatography (HPLC), mass spectrophotometry coupled with HPLC (MS-HPLC), enzyme linked immunosorbent assay (ELISA), and immunohistochemistry (IHC). In some embodiments, combinations of these techniques may also be used.

In a preferred embodiment, pSTAT5 is detected using a flow cytometry based assay, using a labeled anti-phospho-Stat5 antibody comprising a detectable label suitable for detection by FACS analysis, e.g., a fluorescent label such as phycoerythrin (PE) or allophycocyanin (APC).

In embodiments, the disclosure provides a rapid flow-cytometry based assay for detecting TSLP-responsive cells in whole blood. The method is graphically depicted in FIG. 9. The method can advantageously be performed in about 4-5 hours from the time of blood draw. The method comprises obtaining a sample of whole blood from the subject, isolating a CD4+ T cell fraction from the whole blood, culturing the CD4+ T cells in vitro and stimulating with TSLP to induce TSLP-dependent signal transduction, fixing and staining the stimulated cells, detecting pSTAT5 in the cells using flow cytometry, and determining EGID disease status based upon the percentage of pSTAT5 positive cells detected.

In embodiments, the methods described here may also comprise the detection of IL-5 and IL-13 cytokine expression, for example by assaying for the secreted cytokines in the medium of in vitro cultured cells, or by assaying for cytokine gene or protein expression. Protein expression can be determined by various methods, including flow cytometry, chromatography based techniques and solid or liquid phase immunoassays, and combinations thereof, as described above. Gene expression can be determined, for example, using a polymerase chain reaction (PCR) based method, including a reverse transcription PCR reaction (RT-PCR), a flow cytometry based method, including microfluidics assisted fluorescence in situ hybridization (FISH), or a chromatographic technique such as Northern blotting.

The cells used in the assays for TSLP-induced cytokine activation and expression described here are obtained from a sample of whole blood obtained from a human subject in need of therapy for EGID, or who presents with clinical symptoms consistent with EGID, as described in more detail below. The term "whole blood" refers to a sample of blood containing cells, such as red blood cells (also referred to as erythrocytes), white blood cells, and platelets, as well as plasma, which is the liquid remaining after the cells are removed. In the context of the present methods, whole blood is obtained from a subject and assayed for the presence of TSLP-responsive CD4+ T cells. In some embodiments, the CD4+ T cells are memory T cells. In some embodiments, the CD4+ T cells are isolated from the peripheral blood mononuclear cell (PBMC) fraction of the whole blood. In other embodiments, the assays are performed using the PBMC fraction, without isolating the CD4+ T cells. The term "peripheral blood mononuclear cells" (PBMC) refers to the fraction of white blood cells in whole blood that contain a round nucleus and includes lymphocytes (T cells, B cells, natural killer cells) and monocytes. Other white blood cells, referred to generally as granulocytes, have multi-lobed nuclei and include neutrophils, basophils, and eosinophils.

In embodiments, the methods may comprise a step of obtaining whole blood from a subject, e.g., by phlebotomy. The blood collected is preferably venous blood which may be collected into a suitable container, e.g., a container comprising sodium heparin.

In embodiments, the methods may comprise a step of isolating a PBMC fraction from whole blood, for example by a method comprising density centrifugation, e.g., using Ficoll™ or similar reagent. The PBMC fraction, CD4+ T cells, or memory CD4+ T cells may also be isolated, for example, using a negative depletion or positive selection strategy, either in combination with density centrifugation or without a centrifugation step. In negative depletion, non-target cells are tagged with an affinity label which allows for their removal via an affinity reagent, such as an affinity column or similar device. Typically labeling for a negative depletion strategy is accomplished using labelled antibodies against a cell surface antigen located on the non-target cells, i.e., the cells which are to be depleted from the sample, thereby leaving a sample enriched in the target cell population. In positive selection, target cells are tagged with an affinity label and then separated from other non-target cells. Examples of suitable labels include magnetic beads and polyhistidine tags. In embodiments, a combination of one or more of density centrifugation, affinity chromatography, and flow cytometry, for example using an anti-CD4 receptor antibody and/or an anti-CD45 receptor antibody comprising a detectable label, may be used to isolate the PBMC fraction, the CD4+ T cell fraction, and/or the memory CD4+ T cell fraction from whole blood.

The methods described here comprise activating isolated cells in vitro with TSLP in order to induce TSLP-dependent signal transduction in the cells. Generally, the amount of TSLP used will be in the range of about 25-100 ng/ml in serum free medium. The time of activation with TSLP will vary depending on the nature of the downstream effector molecule to be detected. For example, where pSTAT5 is to be detected, very short time periods of TSLP stimulation are required, since activation of STAT5 via phosphorylation is an early event in TSLP-dependent signal transduction. In other case, longer periods of stimulation may be required, for example where cytokine gene expression is to be determined, or cytokine protein expression. The longest time periods are required where the analyte is secreted protein. In exemplary embodiments, the method comprises stimulating the cells with TSLP, e.g., about 25-100 ng/ml TSLP, for about 10-60 minutes, e.g., about 10, 20, 30, 45, or 60 minutes, preferably about 20 minutes for the detection of pSTAT5. The time period for mRNA and protein detections is 3-4 days.

In embodiments, the methods described here comprise determining whether the amount of one or more of the analytes, i.e., pSTAT5, IL-5, or IL-13, is above or below a predetermined diagnostic threshold, wherein the amount relative to the diagnostic threshold indicates EGID disease status, for example the absence of EGID, active EGID, or EGID in remission. In embodiments, an amount of analyte above the diagnostic threshold indicates active EGID in a method for diagnosing, or disease progression in a method of monitoring EGID. In embodiments, the analyte may be the number of CD4+ T cells positive for one or more of pSTAT5, IL-5 mRNA, or IL-13 mRNA. In embodiments, the analyte may be the amount of a cytokine produced by the CD4+ T cells, as measured by mRNA or protein expression, or secreted protein. The diagnostic threshold for each analyte is predetermined based on the amount of the analyte in representative populations of healthy disease-free subjects and subjects in one or more disease categories, for example active EoE, EoE in remission, and Celiac disease with EoE. In embodiments, the performance of the method is measured using an area under the curve (AUC) receiver operating characteristics (ROC) curve.

In accordance with the methods related to EGID disease monitoring, a reduction in the amount of one or more analytes as described herein, i.e., pSTAT5, IL-5 or IL-13, compared to a baseline measurement for the patient, for example as determined at the start of therapy or before the initiation of therapy, or compared to a predetermined diagnostic threshold, indicates that the EGID is being managed by the current therapy. For example, a reduction in one or more of pSTAT5, IL-5 or IL-13 may be indicative of an absence of exposure to food allergens where the therapy comprises an elimination diet, or inhibition of Th2 cytokine production where the therapy comprises glucocorticoid treatment. Likewise, where the amount of one or more of the analytes increases relative to a baseline measurement or predetermined diagnostic threshold, it indicates that the EGID therapy is not effectively managing the disease. In embodiments, the methods may further comprise adjusting a subject's EGID therapy based on the assay result.

In accordance with the methods described here, a human subject in need of treatment for an EGID may include one who has not yet been diagnosed with EGID but who presents with clinical symptoms of EGID. In embodiments, the subject in need presents with one or more clinical features selected from dysphagia, vomiting, food impaction, abdominal pain, refractory reflux symptoms, failure to thrive in young children, a diagnosis of an atopic allergic disorder, and a family member having an EGID diagnosis. In embodiments, the atopic allergic disorder is selected from food allergy, asthma, atopic dermatitis, allergic rhinitis and allergic conjunctivitis.

In addition, a human subject in need of treatment for an EGID may include one who has been diagnosed with EGID and is in need of disease monitoring, for example in order to evaluate the efficacy of an EGID therapy. In embodiments, the methods may also comprise a step of treating the subject diagnosed with EGID, and/or modifying the therapy of a subject undergoing monitoring, as described in more detail below.

In accordance with the methods described here, the subject may be treated with one or more EGID therapies, including, for example, proton pump inhibitor therapy, dietary therapy, anti-cytokine therapy, anti-ALOX15 therapy, anti-TSLP therapy, anti-eosinophil therapy, glucocorticoid therapy, and esophageal dilation. In the context of the present disclosure, the terms "treatment", "treating", or "treat" describe the management and care of a human subject for the purpose of combating EGID and may include the administration of a therapeutic agent as well as the administration of a therapy such as a restricted diet, including for example elemental and elimination diets, or a medical procedure such as esophageal dilation, to alleviate one or more symptoms or complications of EGID, such as EoE or EG, or to eliminate one or more symptoms or complications of EGID, thereby treating the EGID. Therapeutic agents may include small molecules, such as proton pump inhibitors and glucocorticoids, or biologic agents, such as therapeutic antibodies or nucleic acids, including interfering RNAs.

Proton pump inhibitor (PPI) therapy may include treatment with a PPI such as dexlansoprazole, esomeprazole, lansoprazole, omeprazole, pantoprazole, and rebeprazole.

Dietary therapy may include, for example, elemental and elimination diets.

Anti-cytokine therapy may include, for example, a biologic agent targeted to inhibit cytokine signaling by one or more cytokines via their cognate receptors. In embodiments, the anti-cytokine therapy is an anti-T helper type 2 (Th2) therapy. A Th2 immune response is generally characterized by the production of interleukin-4 (IL-4), interleukin-5 (IL-5), and interleukin-13 (IL-13). Accordingly, an anti-Th2 therapy encompasses a therapy targeting one or more of IL-4, IL-5, and IL-13, and/or their receptors in order to inhibit IL-4, IL-5, and/or IL-13 mediated signal transduction. The most common biologics for anti-cytokine therapy are antibodies, preferably monoclonal antibodies, and most preferably fully human or humanized monoclonal antibodies. In embodiments of the methods described here, the anti-cytokine therapy is an anti-T helper type 2 (Th2) therapy selected from one or more of a therapy targeting the IL-4 and/or IL-13 signaling pathway, and a therapy targeting the IL-5 signaling pathway.

Interleukin-4 and interleukin-13 both mediate inflammation through their receptors, with IL-13 also binding to type 2 IL-4 receptors. IL-4 and IL-13 signaling pathways thus overlap and therapies envisioned by the methods described here may target one or both of these signaling pathways. Therapies targeting IL-4 signaling include monoclonal antibodies such as dupilumab, which targets the IL-4 receptor alpha (IL-4Ra). Therapies targeting IL-13 signaling include monoclonal antibodies such as RPC4046 or tralokinumab, both of which target IL-13.

Interleukin-5 (IL-5, CD125) is an eosinophil growth, activation, and survival factor. Humanized anti-IL-5 antibodies have been shown to be effective in treating asthma patients with the severe eosinophilic form of the disease, as discussed in Rothenberg M E., Cell 2016; 165(3): 509. Therapies targeting the IL-5 signaling pathway include, for example, therapies targeting IL-5 and its receptor, also known as CD125. Such therapies include monoclonal antibodies such as mepolizumab and reslizumab, which target IL-5, and monoclonal antibodies such as benralizumab, which target the IL-5 receptor.

Anti-ALOX15 therapy is therapy directed at suppressing the expression or activity of the ALOX15 gene product, arachidonate 15-lipoxygenase. Examples of ALOX15 inhibitors include PD146176.

Anti-TSLP therapy may take the form of immunotherapy, for example using an antibody against TSLP, such as tezepelumab. Corren J., et al., New Engl. J. Med. 2017; 377(10): 936-946.

Anti-TSLP therapy or anti-ALOX15 therapy may also comprise the administration of a single or double stranded ribonucleic acid (RNA) agent that inhibits the expression of the TSLP gene or the ALOX15 gene, for example, by catalyzing the post-transcriptional cleavage of the target mRNA, or by inhibiting transcription or translation of the target mRNA. In embodiments, the RNA agent is a double stranded or single stranded RNA interference-based agent (RNAi). The RNAi agent may be based on a microRNA (miRNA), a short hairpin RNA (shRNA), or a small interfering RNA (siRNA). The RNAi agent comprises a region that is at least partially, and in some embodiments fully, complementary to the target RNA. Although perfect complementarity is not required, the correspondence should be sufficient to enable the RNAi agent, or its cleavage product in the case of double stranded siRNA or RNAi agents comprising cleavable linkers, to direct sequence specific silencing of the target mRNA, e.g., by RNAi-directed cleavage of the target mRNA.

Glucocorticoid therapy may comprise, for example, therapy with one or more glucocorticoids selected from fluticasone, prednisone and budesonide.

The methods of the present disclosure are preferably applicable to human subjects, also referred to as "patients", but the methods may also be applied to other mammalian subjects. Accordingly, in embodiments a method described here may be performed on a "subject" which may include any mammal, for example a human, primate, mouse, rat, dog, cat, cow, horse, goat, camel, sheep or a pig. Preferably, the subject is a human. The term "patient" refers to a human subject.

Examples

Figure 1B:
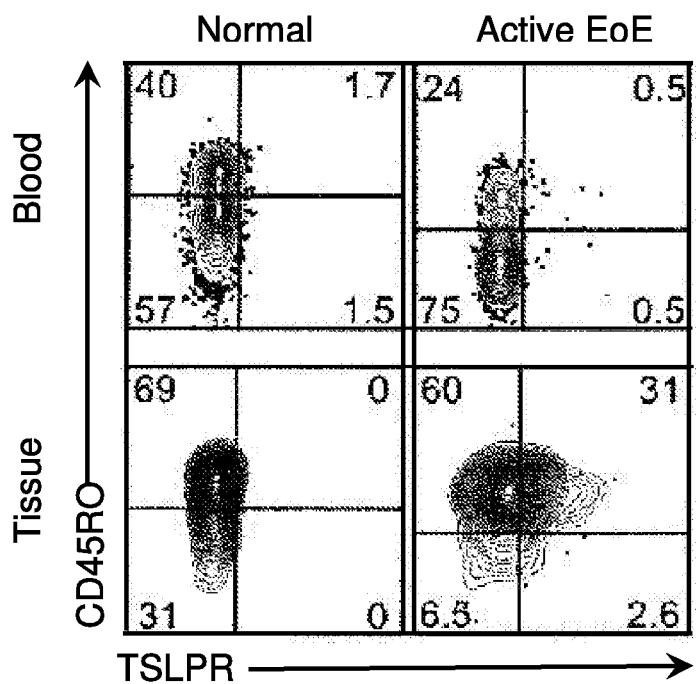

Example 1: A TSLP Responsive Subpopulation of Human Memory CD4$^+$ T Cells is Present in Human Blood of Patients with EGID We sought to determine whether there was a blood and tissue specific T-cell phenotype in patients with active EoE that could be exploited for disease detection, diagnosis, treatment and monitoring. We first performed a polychromatic fluorescence activated cell sorting (FACS) analysis on CD4+ and CD8+ T cells isolated from normal (NL), EoE remission (R), and active EoE (A) esophageal tissue biopsies to detect the expression of a panel of cytokine receptor genes. For all experiments, 'normal' donors were defined as healthy individuals that did not have a history of EoE or other allergic disorders. As shown in FIG. 1A, TSLP receptor (CRLF2/TSLPR) expression was enriched in CD4$^+$ T cells of esophageal tissue and this expression was elevated in CD4+ T cells of tissue from patients with active EoE compared to both normal tissue and tissue from patients in remission, but TSLP receptor expression was not detectable in CD4+ or CD8+ T cells isolated from blood. The flow cytometry double plot shows that TSLP receptor expression in CD45RO$^+$ T cells was significantly increased in the tissue biopsies of active EoE patients compared to normal tissue, but this increase was undetectable in CD45RO$^+$ T cells isolated from blood (FIG. 1B).

Figure 2B:
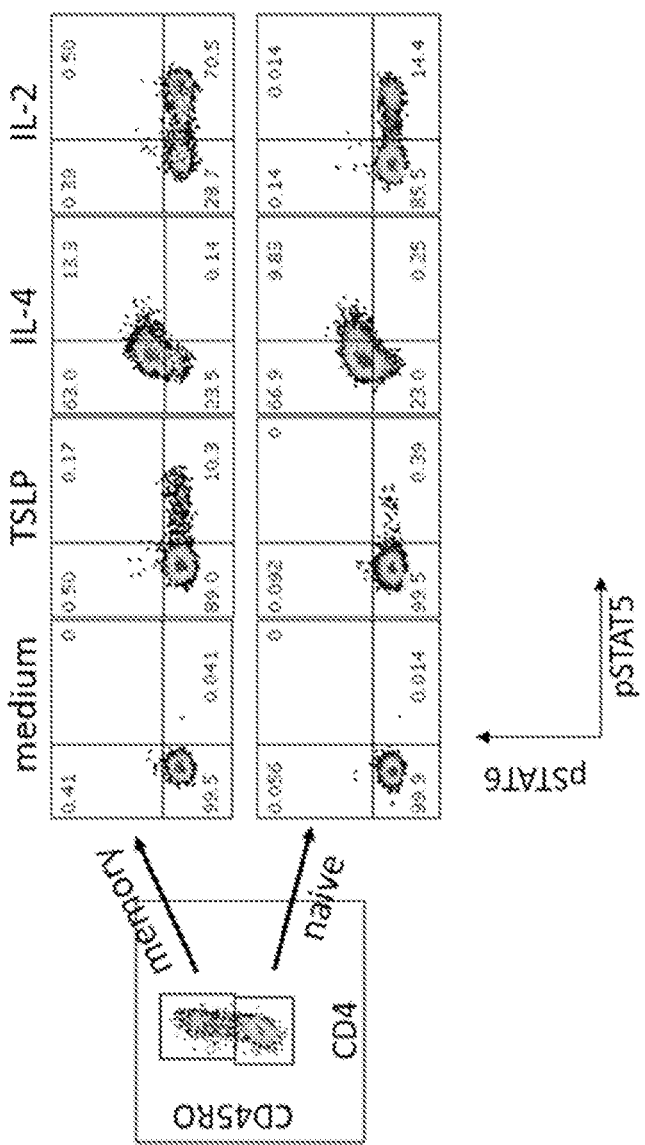
FIGS. 2A-C: A, schematic of cytokine stimulation of human $CD4^+$ T cells isolated from blood. Cells were stimulated for 20 minutes with the indicated cytokine, TSLP, IL-2, or IL-4 and assayed for cytokine responsiveness. Responsiveness to IL-4 was assayed by detection of phosphorylated STAT6 (pSTAT6) and to IL-2 or TSLP by detection of phosphorylated STAT5 (pSTAT5). B, flow cytometry plots showing (left most panel) separation of naïve from memory CD4+ T cells via expression of CD45RO and the percentage of either memory (top four panels) or naïve (bottom four panels) CD4+ T cells detected as positive for either pSTAT6 or pSTAT5 under the indicated conditions of no cytokine stimulation (medium) or stimulation with each of TSLP, IL-4, or IL-2. C, flow cytometry plots showing the percentage of pSTAT5 and pSTAT6 positive memory CD4+ T cells in blood obtained from healthy donors (Normal) and patients with active EoE (Active EoE) following either no stimulation (medium) or in vitro stimulation with TSLP (TSLP).
Figure 2A:
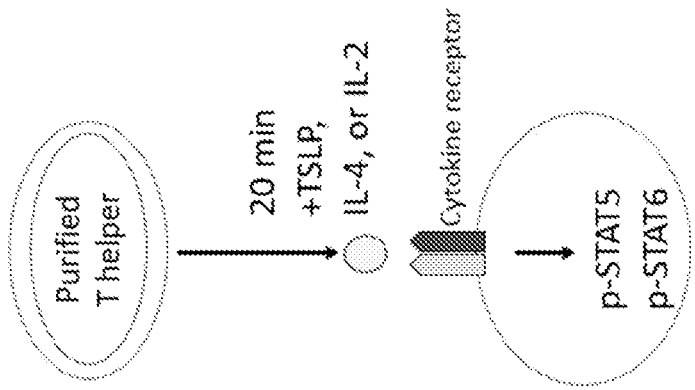
Figure 2C:
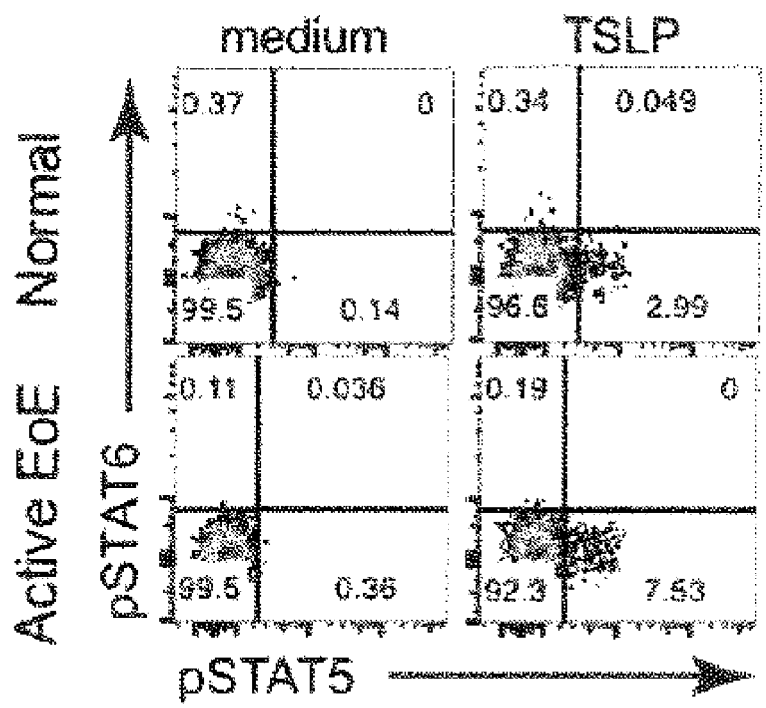

The failure to detect a difference in TSLP receptor expression in cells isolated from blood may have been a result of its much lower expression in CD4+ T cells of the blood as compared to tissue resident CD4+ T cells. We hypothesized that a downstream effector molecule of the TSLP-induced signaling pathway might be expressed at high enough levels to be used as a surrogate for TSLP-responsiveness. Since the phosphorylation of STAT5 is an early event in the activation of TSLP-induced signaling, we sought to determine whether phosphorylated STAT5 (pSTAT5) could be used as a biomarker for TSLP response in CD4+ T cells isolated from blood. FIG. 2A shows a schematic representation of the assay in which human CD4+ T cells were purified from whole blood of healthy or EoE donors and then stimulated for 20 min with either TSLP, IL-4, or IL-2, the latter two cytokines serving as positive controls for responsiveness to IL-4 as indicated by pSTAT6 and responsiveness to IL-2, as indicated by pSTAT5. In addition, we used CD45RO to separate the CD4+ T cells into naïve (CD45RO−) and memory (CD45RO+) subpopulations. The responsiveness of CD4+ T cells to TSLP was measured as the percentage of pSTAT5 positive cells detected following either no treatment or stimulation with TSLP, IL-4, or IL-2 (FIG. 2B). Surprisingly, we found that only the memory T cell subpopulation, and not the naïve T cells, responded to TSLP as measured by the percentage of pSTAT5 positive cells (compare top (memory) and bottom (naïve) rows of panels in FIG. 2B). In contrast, both memory and naïve CD4+ T cells responded to both IL-4 (pSTAT6+) and IL-2 (pSTAT5+). This experiment demonstrated that we could detect TSLP responsive CD4+ T cells in human blood by stimulating the cells in vitro with TSLP and assaying for pSTAT5 positive cells, and that the responsive cells were the memory T cell subpopulation. We next evaluated whether there was a detectable difference in TSLP responsiveness in memory CD4+ T cells isolated from the blood of subjects with active EoE compared to those from healthy (normal) donors. FIG. 2C shows that there was a significant increase in the percentage of TSLP-responsive cells from patients with active EoE compared to those obtained from normal donors.

Figure 3A:
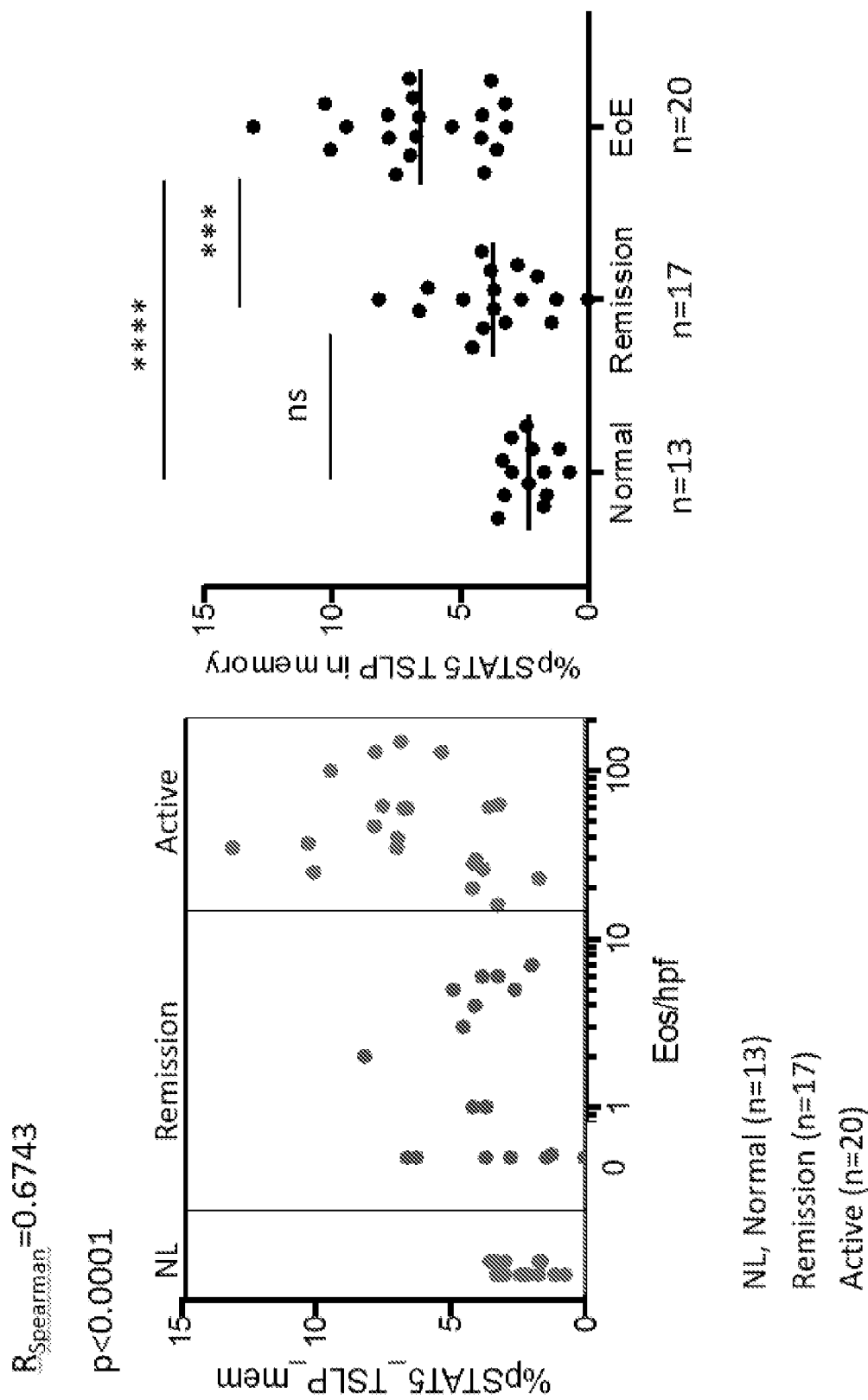
FIG. 3A-D: A, TSLP responsiveness measured as the percentage of pSTAT5 positive memory CD4+ T cells following in vitro stimulation with TSLP of cells obtained from the blood of healthy donors (Normal or NL), EoE patients in remission (Remission), or EoE patients with active disease (EoE or Active) positively correlates with the number of eosinophils per high power field (Eos/HPF) determined from tissue biopsies. In contrast, a poor correlation is seen with responsiveness to IL-4 as measured by the percentage of pSTAT6 positive (B) or pSTAT5 positive (C) naïve or memory CD4+ T cells following in vitro stimulation with IL-4. D, no correlation is observed between responsiveness to IL-2 as measured by the percentage of pSTAT5 positive naïve or memory CD4+ T cells following in vitro stimulation with IL-2.
Figure 3B:
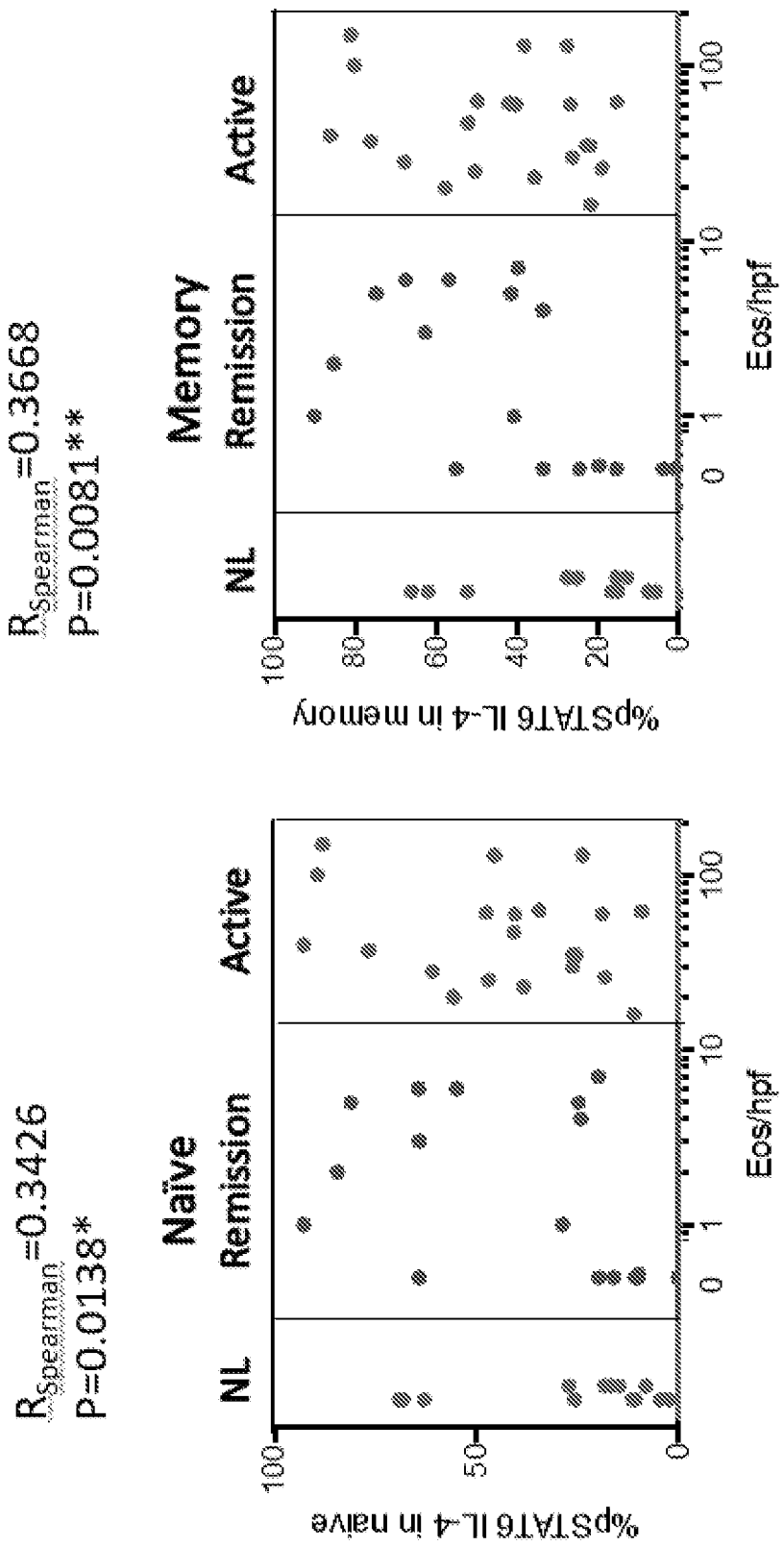
Figure 3C:
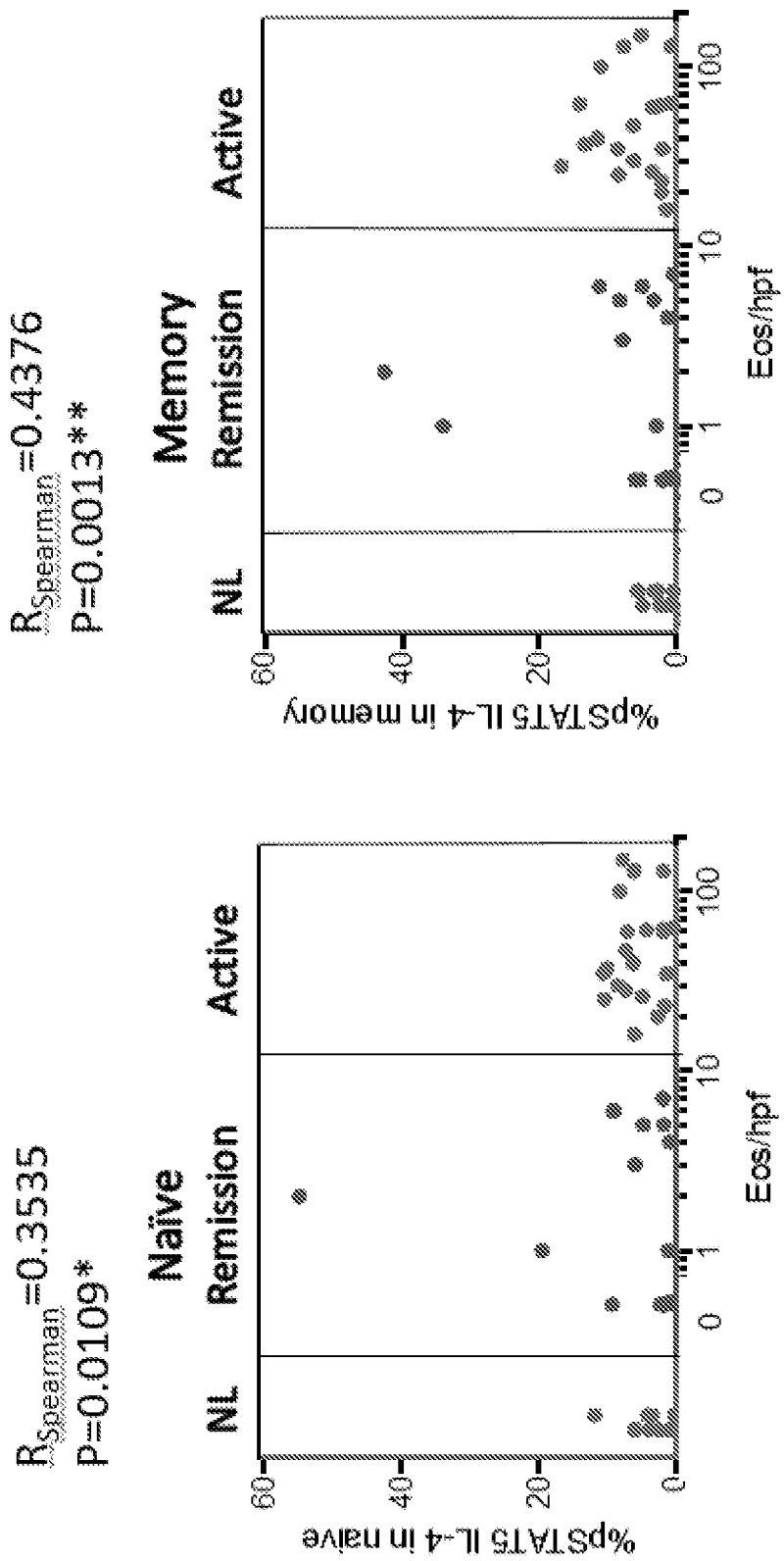
Figure 3D:
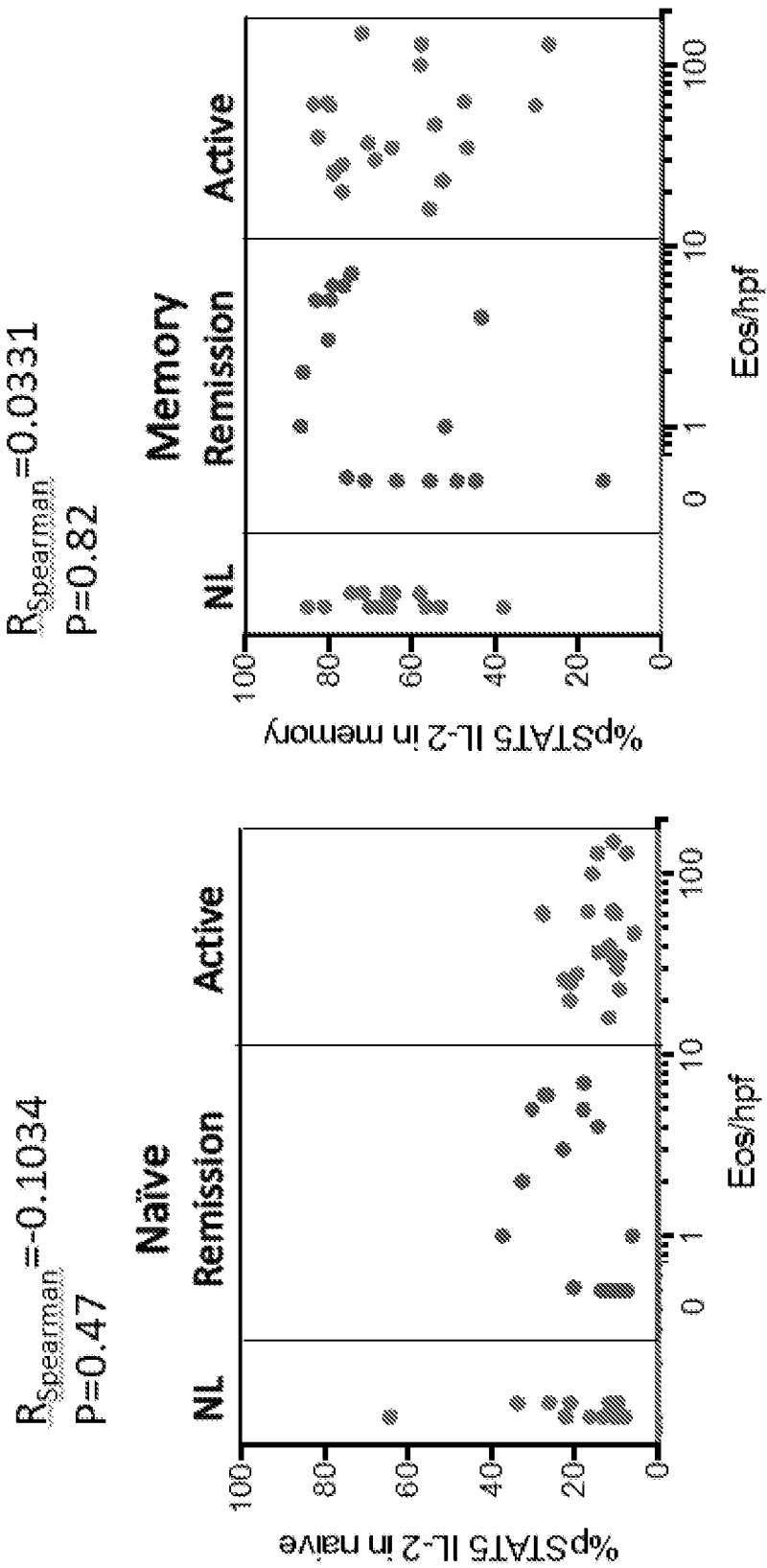

We next examined whether there was a correlation between the percentage of TSLP-responsive memory Th cells (pSTAT5+ CD45RO+ CD4+) and tissue eosinophil levels (EOS/HPF), which is the standard benchmark for EoE diagnosis and the only EoE severity monitoring parameter currently available. Dellon E S., Gastroenterol. Hepetol. NY 2011 7(11):742-744. As shown in FIG. 3A, the TSLP responsiveness of memory Th cells isolated from whole blood, as measured by percentage of pSTAT5 positive cells, was positively correlated with the number of eosinophils per high power field (EOS/HPF), as determined by analysis of esophageal tissue biopsies, in each of the categories of subject evaluated, healthy donors, EoE patients in remission, and patients with active EoE. Patients with active EoE, defined as having at least 15 EOS/HPF, exhibited a significant increase in the percentage of pSTAT5 positive cells compared to normal donors. Notably, patients in EoE remission, defined as having 2-14 EOS/HPF, showed a moderate elevation in percentage of pSTAT5 positive cells, indicating a non-normalized Th compartment in the disease remission state (p<0.001, remission vs. EoE). In contrast, there was only a poor correlation between EoE status as measured by EOS/HPF and the responsiveness of memory or naïve CD4+ T cells to IL-4 as measured by the percentage of pSTAT6 (FIG. 3B) or pSTAT5 (FIG. 3C) positive cells. Further, there was no correlation for IL-2 responsiveness, as measured by pSTAT5 positive cells (FIG. 3D). Taken together, these results indicate the pSTAT5 provides a suitable biomarker for measuring TSLP-responsive cells obtained from whole blood, and that there is a strong correlation between this biomarker and EGID disease status, making it an attractive candidate for a clinical assay.

Figure 4A:
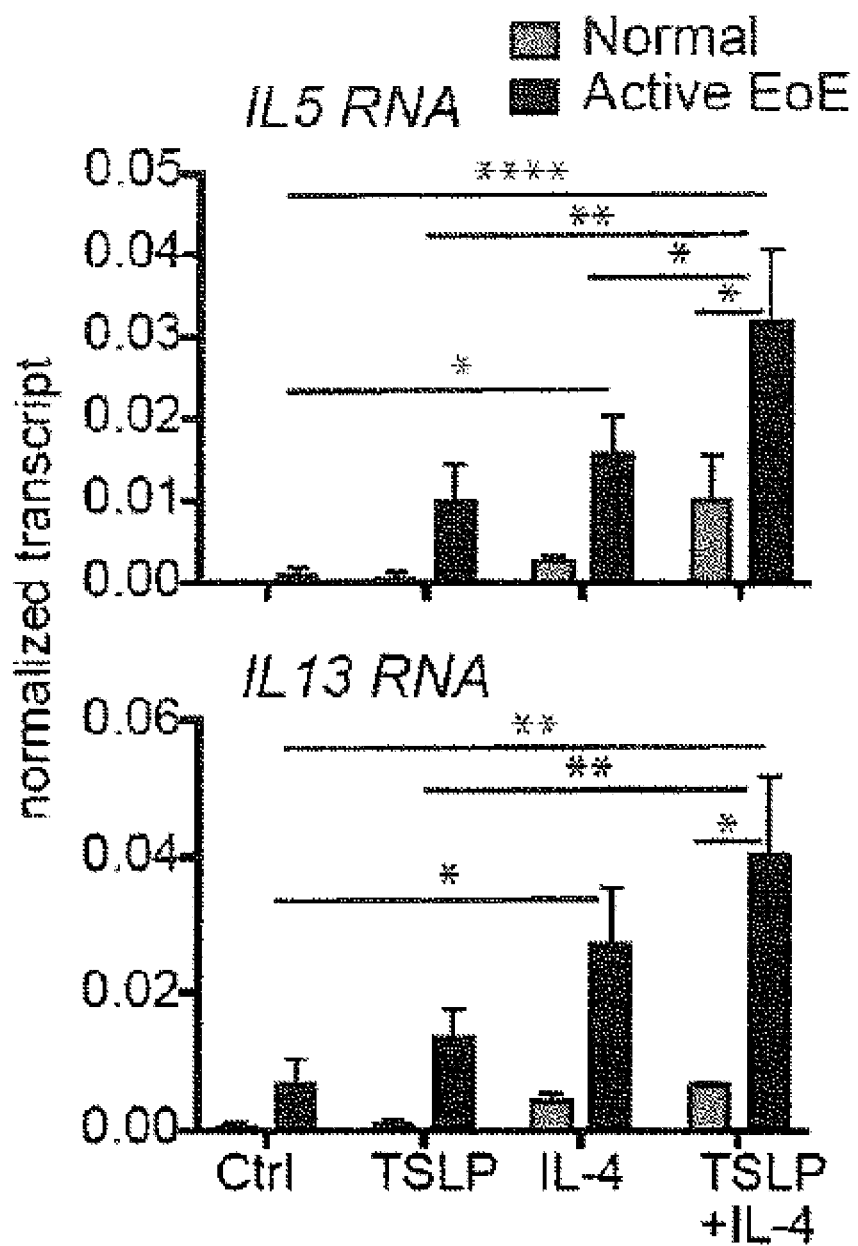
FIG. 4A-B: $CD4^+$ T cells were isolated from healthy subjects (normal, light bars) and patients with active EoE (Active EoE, dark bars) and either left unstimulated (Ctrl) or stimulated with either TSLP, IL-4, or both TSLP and IL-4 for 3 days then analyzed for (A) gene expression of IL-5 (top panel) and IL-13 (bottom panel) using RT-PCR to quantitate mRNA levels, or (B) IL-5 protein secretion using ELISA. Mean+/−SEM.
Figure 4B:
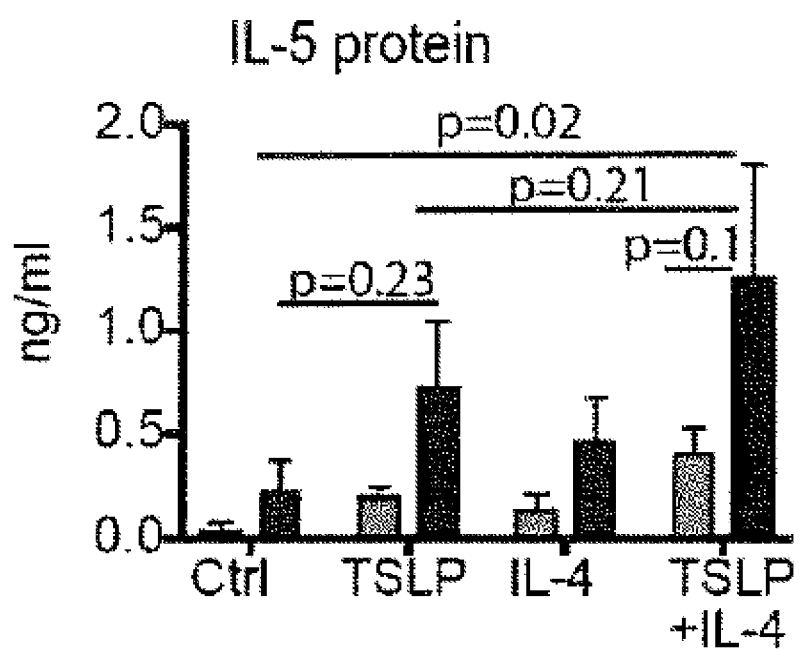

In further experiments, we confirmed that the cells characterized as TSLP-responsive based on pSTAT5 also elicit de novo synthesis of Th2 cytokines IL-5 and IL-13, evidencing that the in vitro TSLP response observed in our assays represents a true activation of the proinflammatory pathway regulated by TSLP. The results of this study are shown in FIG. 4. CD4+Th cells were isolated from the blood of normal healthy (NL) donors and patients with active EoE. Cells were cultured in vitro and activated by exposure to anti-CD3 and anti-CD28 antibodies and IFNγ depletion in the presence of IL-4 and/or TSLP for 3 days, then assayed for the expression of IL5 and IL13 mRNA (FIG. 4A) and IL-5 protein (FIG. 4B). Both TSLP and IL-4 induced the expression of IL5 and IL13 mRNA in CD4+Th cells isolated from patients with active EoE, but not in cells isolated from normal donors. Co-stimulation with both TSLP and IL-4 further increased the expression of these cytokines in the cells from active EoE patients, but only mild expression of these cytokines was detected in cells from healthy donors. IL-5 protein expression was also differentially increased in the CD4+Th cells isolated from patients with active EoE, compared to those isolated from normal donors.

Figure 5A:
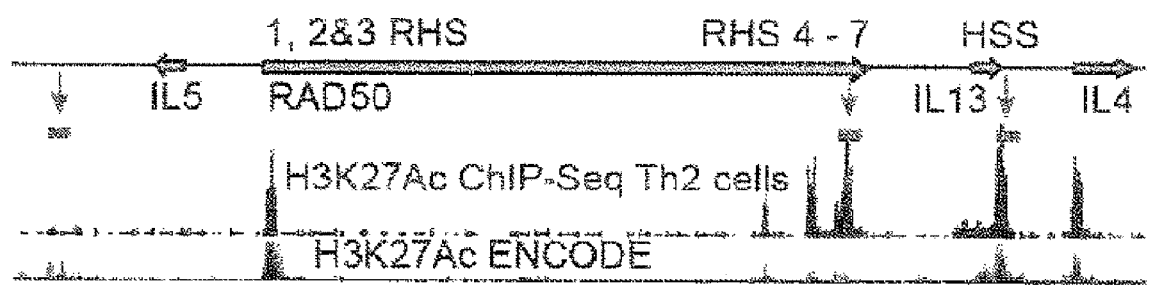
FIGS. 5A-B: (A) PCR primer design for H3K27Ac-ChIP-PCR. Three sets of TaqMan primers (gray rectangles below arrows) were designed based on ChIP-sequence results and ENCODE data. (B) Purified $CD4^+$ T cells from normal donors were activated in the presence or absence of TSLP or IL-4 for 3 days and subjected to ChIP with anti-H3K27Ac. PCR products were normalized to their inputs (5%). Data represent duplicate experiments. Mean+/−SEM.
Figure 5B:
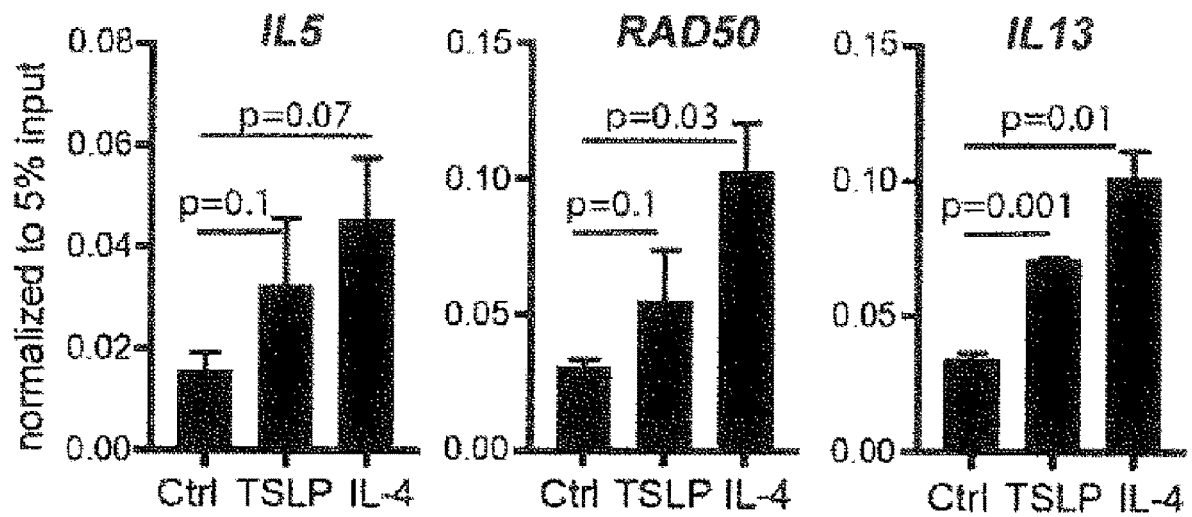

We next examined whether the upregulation of Th2 cytokine expression correlated with epigenetic changes in the chromatin status of the cells, which would be a further indication that the response functions to activate TSLP receptor mediated signal transduction. CD4+Th cells were isolated from normal donors and activated in vitro as described above. Cells were collected and fixed on day 3, followed by chromatin immunoprecipitation (ChIP) coupled with quantitative polymerase chain reaction (PCR) or "ChIP-PCR" analysis for detection of the histone mark H3K27Ac, which indicates areas of active chromatin. The data showed enhanced H3K27Ac downstream of the IL5 gene, in a locus control region in the RAD50 gene (RHS7), and in a hypersensitivity site (HSS) of an IL3 enhancer induced by TSLP (FIG. 5A-B). These results are consistent with previously reported epigenetic signatures of Th2 cytokine loci. Similar chromatin modifications were observed in murine Th2 cells upon TSLP treatment, suggesting an evolutionarily conserved mechanism regulated by TSLP. H3K27Ac changes also correlated with transcription of the IL5 and IL13 genes in the presence of TSLP. Since these changes were observed with in vitro activated CD4+ T cells from normal donors, which we have already determined contain a low percentage of TSLP-responsive cells, we expect a more robust signal of epigenetic modification will be observable in cells from patients with active EoE, making an assay based on chromatin immunoprecipitation coupled with RNA sequencing (ChIP-RNAseq) a highly feasible molecular diagnostic, genome-wide tool for eosinophilic gastrointestinal disease.

Example 2: Blood-Based Diagnostic Assay for EGID

The results described above demonstrate a robust positive correlation between the 'gold standard' diagnostic criterion of disease status, i.e., EOS/HPF in tissue biopsies, and the percentage of pSTAT5 positive cells following in vitro stimulation with TSLP using autologous blood memory CD4+ T cells. This blood-based pSTAT5 assay therefore represents a promising non-invasive alternative to the conventional endoscopic method for detection, diagnosis, and monitoring of EGID.

In order to further validate this method for clinical use, we undertook a larger-scale study. Subjects were divided into three groups: healthy donors, designated as normal (NL); patients with EoE who were in remission; and patients with active EoE. In addition, blood samples were obtained from patients having both Celiac disease and EoE (Celiac+EoE, n=6) and patients with Crohn's disease (Crohn's, n=4), which is a non-allergic autoimmune disorder, as a negative control. TSLP-responsiveness determined as the percentage of memory CD4+ T cells that were also positive for pSTAT5 following in vitro stimulation with TSLP was determined as described above.

Figure 6A:
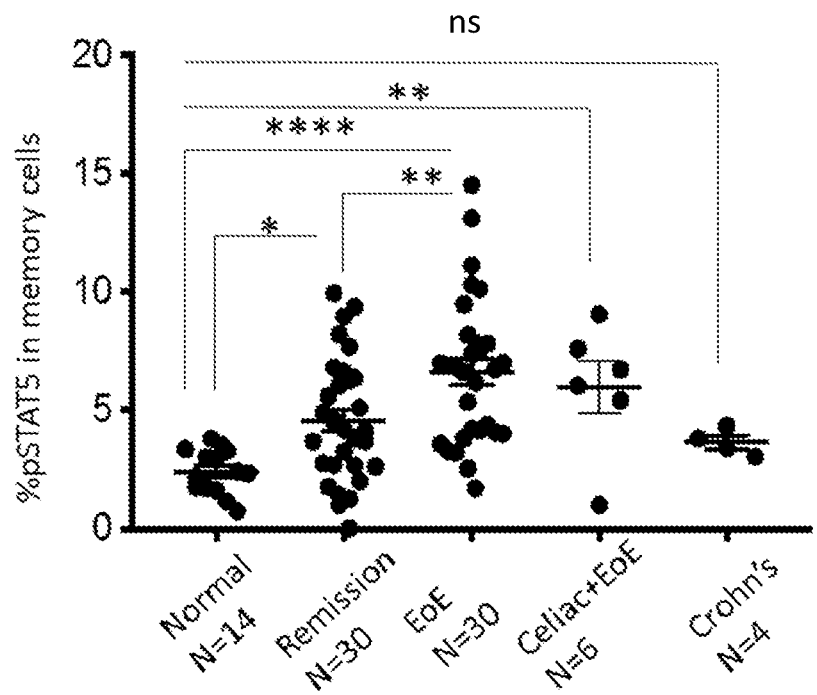
FIG. 6A-F: A, percentage of pSTAT5 positive memory T cells as a percentage of total memory T cells following in vitro TSLP stimulation of cells isolated from the blood of healthy donors (Normal, n=14), EoE patients in remission (Remission, n=30), EoE patients with active EoE (EoE, n=30), patients with Celiac disease and active EoE (Celiac+ EoE, n=6) and patients with Crohn's disease (Crohn's, n=4), which is a non-allergic autoimmune disorder (used as negative control); ROC curves showing sensitivity and specificity of the discrimination between B, normal and EoE remission; C, normal and active EoE; and D, remission and active EoE. E, Comparison of purified $CD4^+$ T cells and unpurified blood cells gated on CD4+ cell population in response to TSLP as percentage of pSTAT5 positive events inside of memory cell population (n=14 pairs). F, Bland-Altman plot shows differences in two methods (purified and unpurified $CD4^+$ T cells) measuring responsiveness of $CD4^+$ T cells to TSLP by STAT5 phosphorylation (n=14 pairs).
Figure 6B:
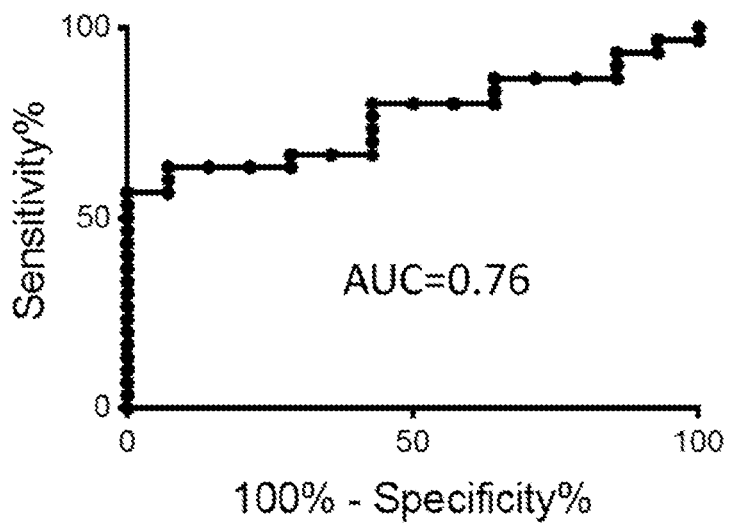
Figure 6C:
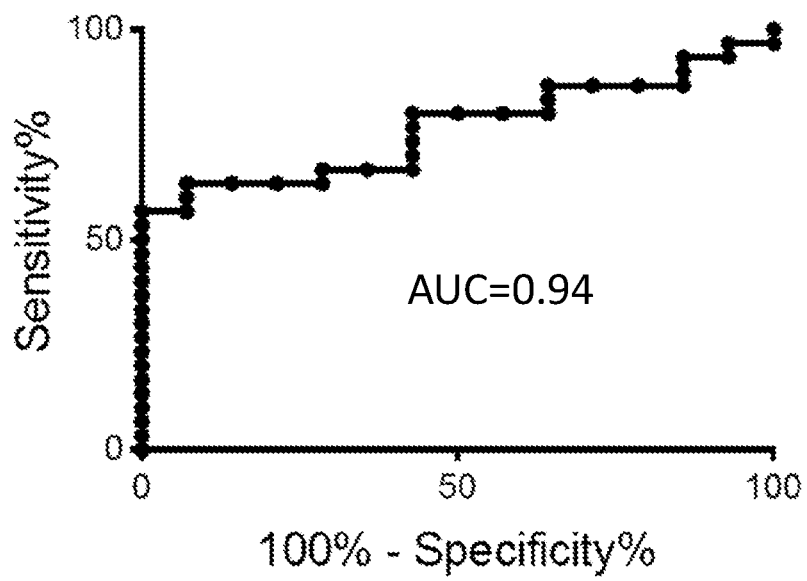
Figure 6D:
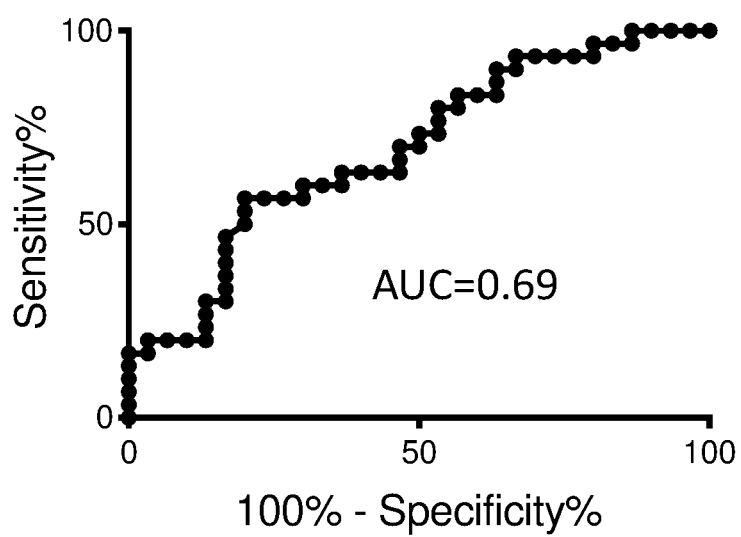
Figure 6E:
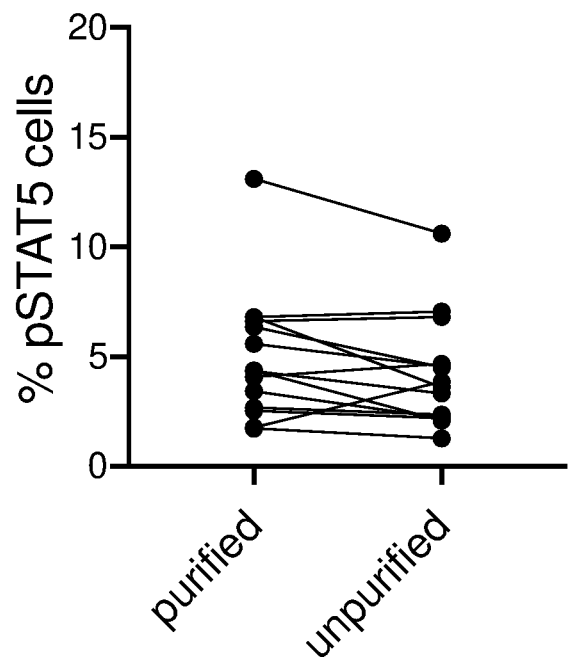
Figure 6F:
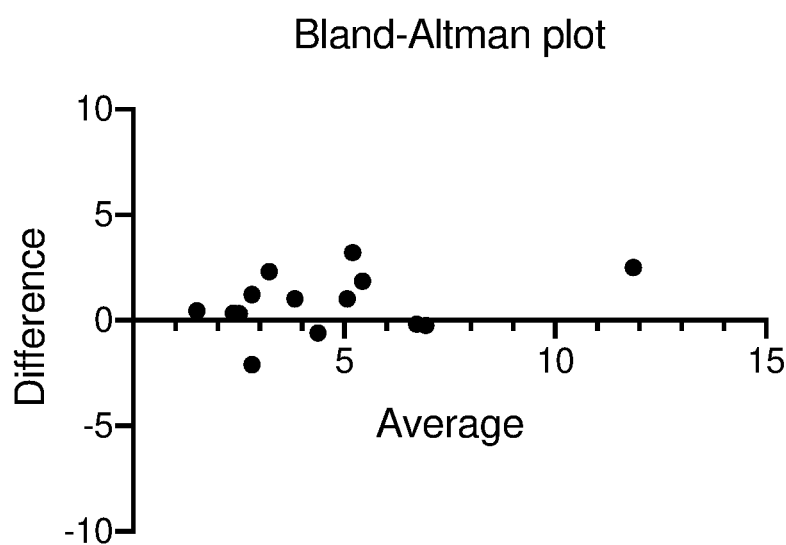

As shown in FIG. 6A, the percentage of memory CD4+ T cells positive for phosphorylated STAT5 (pSTAT5) following in vitro TSLP stimulation was significantly different between (i) healthy donors and EoE patients in remission (*p=0.013), (ii) healthy donors and Celiac patients with EoE (p=0.0063), (iii) health donors and patients with active EoE ( p<0.0001)), and (iv) active EoE and EoE patients in remission (p=0.0056). Patients with Crohn's disease had very low numbers of cells responding to TSLP, similar to the numbers for normal donors. In contrast, patients having both Celiac disease and EoE showed a significantly higher percentage of pSTAT5 positive cells, as did patients with active EoE and EoE patients in remission. These findings demonstrated a specific response of $CD4^+$ T cells to TSLP in patients with eosinophilic gastrointestinal disorders (EGID) as opposed to gastrointestinal autoimmune disorders, such as Crohn's disease. The clinical utility of these results was further validated by receiver operating characteristic (ROC) analysis. Memory $CD4^+$ T cells from EoE patients showed a strong increase in responsiveness to TSLP in the ROC curve data for normal vs. remission (FIG. 6B), as well as for normal (n=14) vs. active EoE (FIG. 6C) and EoE remission vs. EoE active (FIG. 6D). Alternatively, the method without $CD4^+$ T cell isolation was used to detect pSTAT5 induced by TSLP. In this method, PBMCs, which contain variety of cell populations, were stimulated with TSLP for 20 minutes and then subjected to flow cytometry analysis. $CD4^+$ T cells were detected by gating strategy during flow cytometry analysis. In both methods, purified and unpurified $CD4^+$ T cells, blood samples from same donors were used and percent of pSTAT5 positive cells induced by TSLP was compared. Non-significant differences within the group were observed (FIG. 6E-F). Therefore, unpurified $CD4^+$ T cells method could potentially be used. This will potentially further shorten the processing time and reduce the human error generated during the $CD4^+$ purification.

Figure 7A:
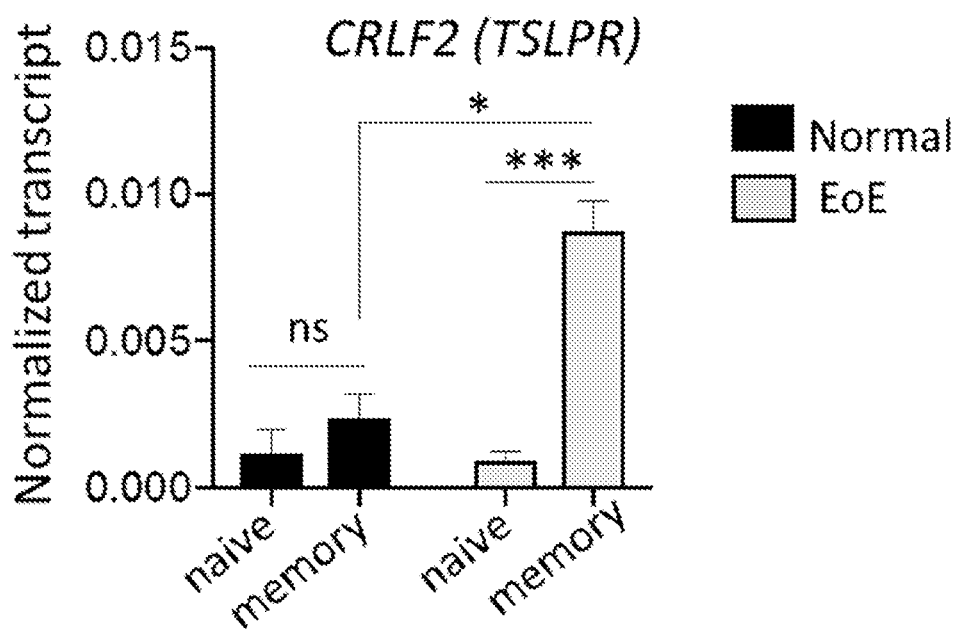
FIGS. 7A-E: mRNA expression of A, CRLF2 (TSLPR), B, IL-5, and C, IL-13 in naïve and memory CD4+ T cells isolated from the blood of healthy donors (normal) and patients with active EoE (EoE) either without (−) or with (+) TSLP stimulation, B, C. Flow cytometry analysis of protein expression for IL-5 and IL-13 (D) or IFNg and IL-4 (E), either without (medium) or with (TSLP) TSLP stimulation.
Figure 7B:
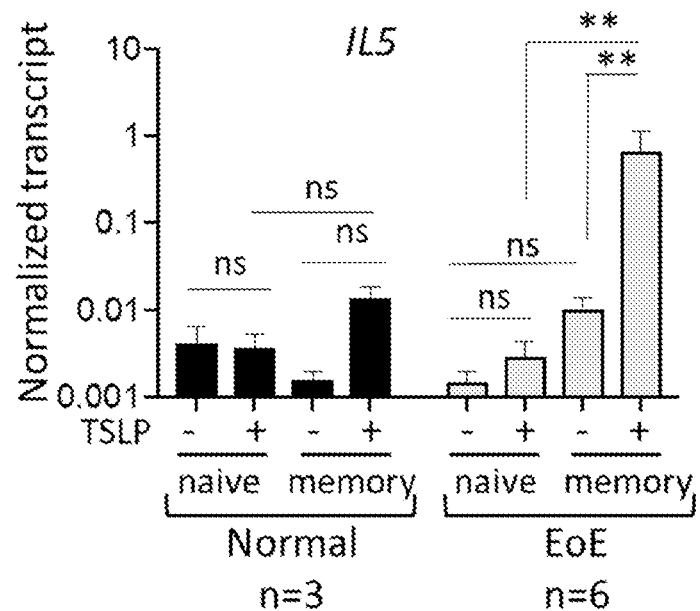
Figure 7C:
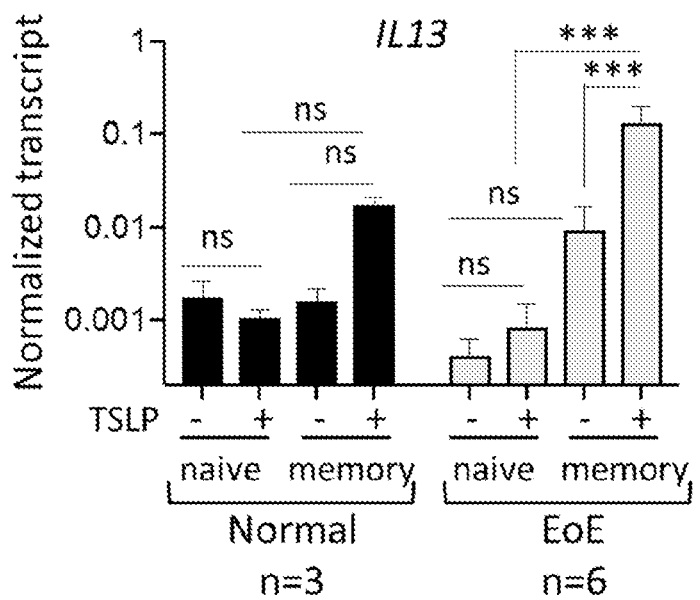
Figure 7D:
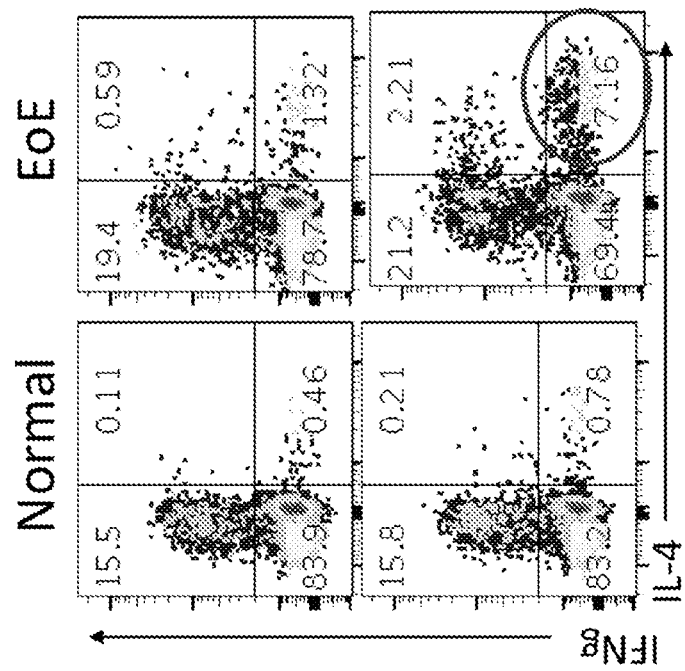
Figure 7E:
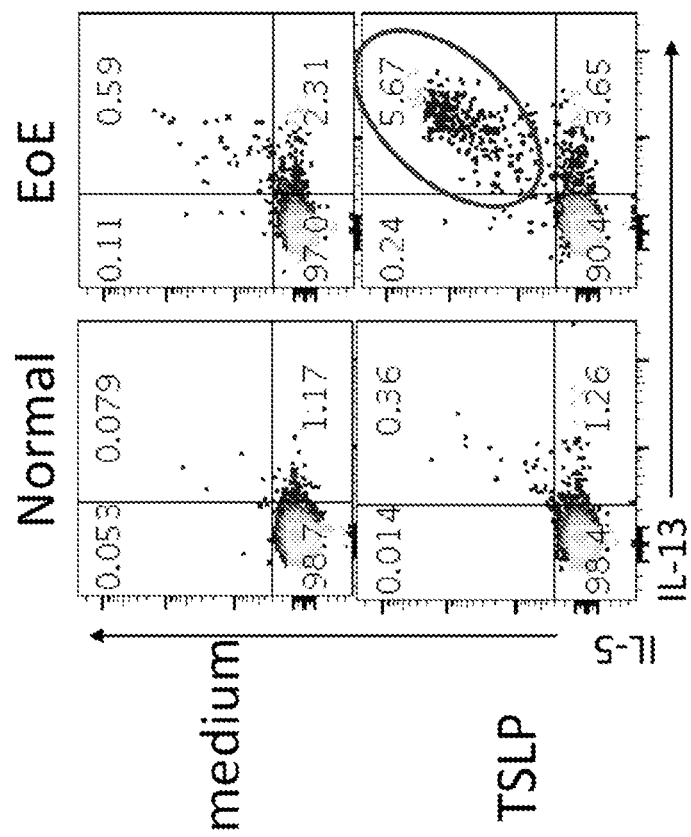

We further validated the biological significance of the observed TSLP responsiveness of $CD4^+$ T cells using a transcription assay to evaluate the gene expression of the TSLP receptor (CRLF2) and the pro-allergic cytokines IL-5, and IL-13. $CD4^+$ Th cells were isolated from the blood of normal and EoE patients and sorted using flow cytometry to differentiate between memory ($CD45RO^+$) and naïve ($CD45RA^-$) CD4+T subpopulations. The expression level of CRLF2/TSLPR mRNA was significantly higher within population of memory cells from EoE individuals compared to naïve cells and memory cells from normal donors (FIG. 7A). The cells were then activated for 3 days in the presence or absence of TSLP. As shown in FIG. 7B-C, memory $CD4^+$ Th cells from patients with active EoE expressed elevated levels of mRNA for each of IL5 (FIG. 7B) and IL13 (FIG. 7C). In addition, the increase in cytokine transcript expression was followed by an increase in protein production of cytokines IL-5 and IL-13 (FIG. 7D) and IL-4, but not IFNγ (FIG. 7E).

Overall, our results show that TSLP receptor expression is upregulated in $CD4^+$ T cells obtained from the blood of patients with active EoE at both the mRNA and protein levels and that TSLP strongly induces both pSTAT5 and the expression of Th2 cytokines downstream of STAT5 activation, IL-5 and IL-13 in these cells.

Example 3: TSLP-Induced Alterations in T-Cell Transcriptomes

To substantiate the finding that TSLP is a Th2 inducer in CD4+ T cells in the blood, we assessed the transcriptional profile of cytokines and other molecules induced by TSLP. To characterize the TSLP-induced transcriptomic changes in an EGID disease context, bulk RNAseq analyses of human blood memory CD4+ T cells was performed using blood obtained from three active EoE patients. In brief, the PBMC fraction was isolated from whole blood (5-10 mL) and the memory CD4+ T cell fraction was isolated and activated in vitro as described above, i.e., by exposure to anti-CD3 and anti-CD28 antibodies and IFNγ depletion in the absence or presence of TSLP for 3 days. Samples were subjected to bulk RNA sequencing and bioinformatics analyses using GENESPRING software.

Figure 8:
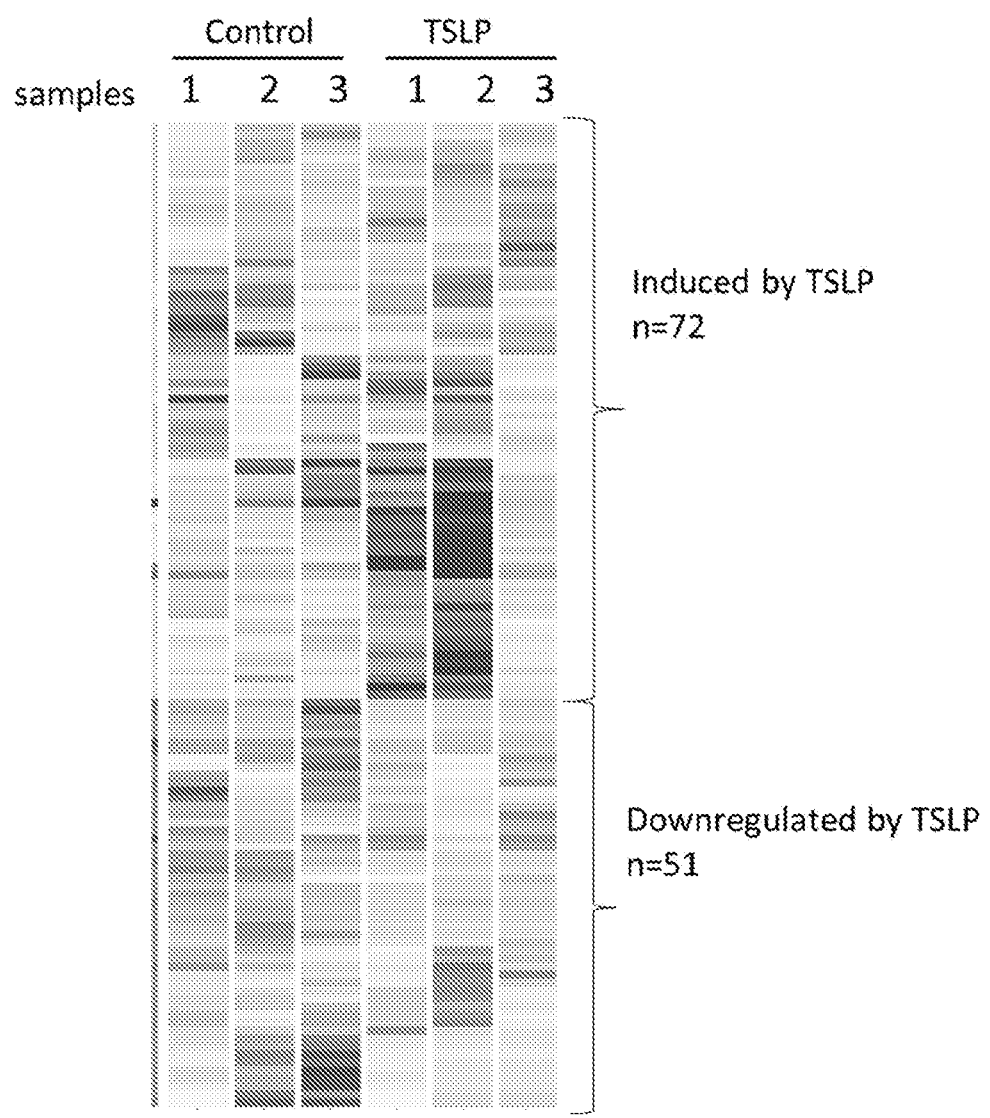
FIG. 8: Heat map showing individual results of expression profiling of memory CD4+ T cells obtained from 3 EoE patients, in the presence or absence of TSLP. Seventy-two transcripts were induced and fifty-one were downregulated by stimulation with TSLP compared to unstimulated.

The results of RNA sequencing are shown in FIG. 8 as a heat map. Samples 1-3 represent memory CD4+ T cells obtained from patients with active EoE. The first three rows show gene expression in unstimulated cells (control) and the next three rows show gene expression in cells stimulated with TSLP (TSLP). In the TSLP-activated memory CD4+ T cells derived from EoE active donors, TSLP induced 72 genes and downregulated 51 genes compared to controls. Many of the upregulated genes are known to be involved in allergic inflammation, which validates the importance of TSLP in initiation of allergic responses.

Example 4: Blood-Based pSTAT5 Assay for EGID

The results presented here indicate that the presence of TSLP-responsive memory T helper cells in peripheral blood can be used as an indicator of EGID status. Although the work presented here was performed in the context of EoE, we believe it is equally applicable to eosinophilic gastritis (EG) and eosinophilic gastroenteritis (EGE) because the majority of EG/EGE patients also have EoE and these EGID involve a similar type 2 allergic response.

Figure 9:
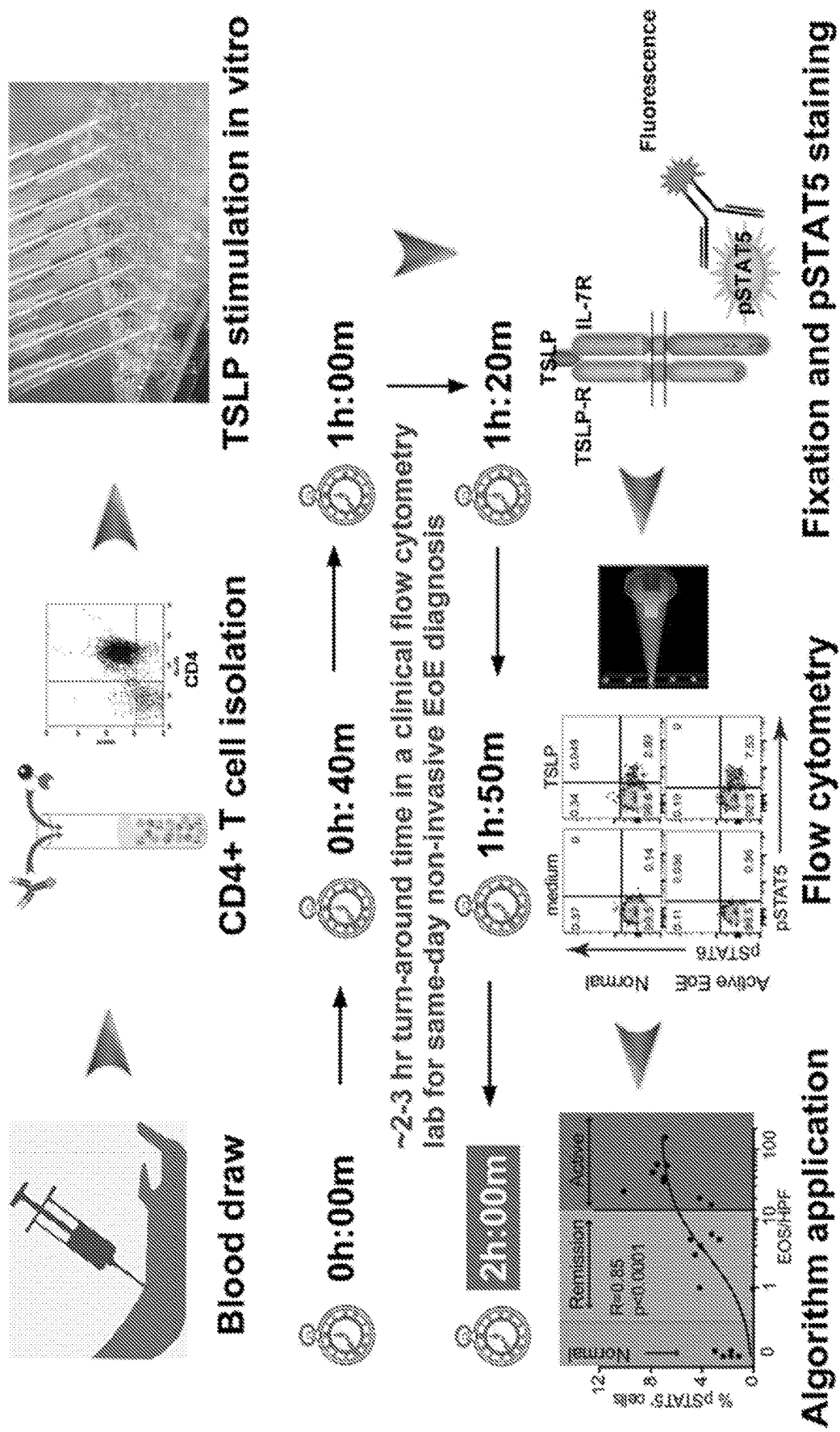
FIG. 9: Schematic depicting diagnostic assay process flow for rapid detection of TSLP responsive cells isolated from whole blood using a flow cytometry based assay.

A schematic depicting an exemplary embodiment of a rapid assay for detection of TSLP responsive cells isolated from whole blood is shown in FIG. 9. The entire process from obtaining a blood sample from a subject to data output and EoE status determination may be performed in about 4-5 hours, including the time for initial isolation of the PBMC fraction from whole blood before CD4+ T cell purification, a TSLP stimulation time of about 20 min, sample preparation for flow cytometry analysis (fixation, permeabilization, staining), and flow cytometric analysis. In this exemplary embodiment, $CD4^+$ T cells are isolated from whole blood, stimulated in vitro with TSLP, followed by fixing and permeabilization of the cells and detection of pSTAT5 using fluorescently-labeled anti-pSTAT5 monoclonal antibodies by flow cytometry. The percentage of pSTAT5 positive $CD4^+$ T cells is determined and compared to a previously determined diagnostic cutoff in order to classify the sample a belonging to a group defined by disease status, e.g., a normal healthy subject, an EoE patient in remission, or an patient with active EoE.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating eosinophilic gastrointestinal disorder (EGID) in a human subject in need thereof, the method comprising
   detecting thymic stromal lymphopoietin (TSLP) responsive cells in a sample of whole blood obtained from the subject by
   contacting cells in vitro with TSLP without stimulation of the cells with anti-CD3 or anti-CD28 antibodies, wherein the cells are selected from PBMC, CD4+ T cells, or memory CD4+ T cells, and
   detecting one or more analytes in the cells or secreted by the cells, the one or more analytes selected from phosphorylated signal transducer and activator of transcription 5 (pSTAT5), interleukin-5 (IL-5), and interleukin-13 (IL-13),
   wherein the detection of the one or more of the analytes indicates TSLP responsive cells in the blood of the human subject,
   determining whether an amount of the one or more analytes is above or below a predetermined diagnostic threshold, wherein an amount above the threshold indicates an EGID status of active disease for the subject and an amount below the threshold indicates that an EGID status of managed, and
   administering an EGID therapy to the subject having an EGID status of active disease, wherein the EGID therapy is selected from proton pump inhibitor therapy, dietary therapy, anti-cytokine therapy, anti-ALOX15 therapy, anti-TSLP therapy, anti-eosinophil therapy, glucocorticoid therapy, and esophageal dilation; or
   re-administering current therapy to the subject having an EGID status of managed.

2. The method of claim 1, for use in a method for diagnosing or monitoring EGID in a human subject in need thereof.

3. The method of claim 1, wherein the method further comprises a step of isolating a fraction of cells from the whole blood enriched for PBMC, CD4+ T cells, or memory CD4+ T cells.

4. The method of claim 1, wherein the analyte is pSTAT5.

5. The method of claim 1, wherein the analyte is IL-5 or IL-13 gene or protein expression.

6. The method of claim 4, wherein the pSTAT5 is detected by a method comprising flow cytometry.

7. The method of claim 5, wherein the IL-5 or IL-13 gene expression is detected by a method comprising a polymerase chain reaction (PCR), flow cytometry, or a chromatographic technique.

8. The method of claim 5, wherein the IL-5 or IL-13 protein expression is detected by a method comprising one or more of flow cytometry, immunoassay, and a chromatographic technique.

9. The method of claim 1, wherein the EGID is eosinophilic esophagitis (EoE) or eosinophilic gastritis (EG).

10. The method of claim 1, wherein the subject in need is characterized as presenting with one or more clinical features selected from dysphagia, food impaction, vomiting, abdominal pain, refractory reflux symptoms, failure to thrive in young children, a diagnosis of an atopic allergic disorder, and a family member having an EGID diagnosis.

11. The method of claim 10, wherein the atopic allergic disorder is selected from food allergy, asthma, atopic dermatitis, allergic rhinitis and allergic conjunctivitis.

12. The method of claim 1, wherein the EGID therapy comprises anti-TSLP therapy.

13. The method of claim 12, wherein the anti-TSLP therapy is an immunotherapy.

14. The method of claim 13, wherein the anti-TSLP therapy comprises anti-TSLP monoclonal antibody therapy.

15. An assay for detecting a thymic stromal lymphopoietin (TSLP) responsive population of cells in human blood, wherein the method is performed within 1-6 hours, the method comprising
    contacting cells in vitro with TSLP, wherein the cells are previously isolated from a sample of whole blood obtained from a human subject in need of treatment for an eosinophilic gastrointestinal disorder (EGID), and
    detecting phosphorylated signal transducer and activator of transcription 5 (pSTAT5) in the cells by a method comprising one or more of flow cytometry, immunoassay, and a chromatographic technique,
    wherein the presence of pSTAT5 indicates a TSLP responsive population of cells in the blood of the human subject,
    wherein the cells are selected from PBMC, CD4+ T cells, or memory CD4+ T cells, and
    wherein the method does not include stimulation of the cells with anti-CD3 or anti-CD28 antibodies.

16. The assay of claim 15, wherein the assay is performed by a method comprising flow cytometric analysis of pSTAT5.

17. The assay of claim 15, wherein the method comprises isolating PBMC, CD4+ T cells, or memory CD4+ T cells from the sample of whole blood.

18. The assay of claim 15, wherein the assay is performed in 2-4 hours.

* * * * *